United States Patent
Gall et al.

(10) Patent No.: US 10,302,663 B2
(45) Date of Patent: May 28, 2019

(54) METHOD OF ASSESSING PANCREATIC BETA-CELL FUNCTION

(75) Inventors: Walter Gall, Raleigh, NC (US); Kay A. Lawton, Raleigh, NC (US)

(73) Assignee: METABOLON, INC., Morrisville, NC (US)

( * ) Notice: Subject to any disclaimer, the term of this patent is extended or adjusted under 35 U.S.C. 154(b) by 1330 days.

(21) Appl. No.: 14/344,655

(22) PCT Filed: Sep. 11, 2012

(86) PCT No.: PCT/US2012/054640
§ 371 (c)(1),
(2), (4) Date: Oct. 23, 2014

(87) PCT Pub. No.: WO2013/039898
PCT Pub. Date: Mar. 21, 2013

(65) Prior Publication Data
US 2015/0065460 A1  Mar. 5, 2015

Related U.S. Application Data

(60) Provisional application No. 61/534,679, filed on Sep. 14, 2011.

(51) Int. Cl.
*G01N 33/50* (2006.01)
*G01N 33/92* (2006.01)
(Continued)

(52) U.S. Cl.
CPC ............ *G01N 33/92* (2013.01); *A61K 31/661* (2013.01); *A61K 31/685* (2013.01); *G01N 33/507* (2013.01); *G01N 33/6893* (2013.01); *G01N 33/5023* (2013.01); *G01N 2500/04* (2013.01); *G01N 2500/10* (2013.01); *G01N 2560/00* (2013.01); *G01N 2570/00* (2013.01); *G01N 2800/042* (2013.01); *G01N 2800/50* (2013.01); *G01N 2800/52* (2013.01); *G01N 2800/56* (2013.01); *Y10T 436/143333* (2015.01); *Y10T 436/173845* (2015.01); *Y10T 436/174614* (2015.01); *Y10T 436/201666* (2015.01)

(58) Field of Classification Search
CPC combination set(s) only.
See application file for complete search history.

(56) References Cited

U.S. PATENT DOCUMENTS 7,700,555 B2    4/2010  Gunton et al.
2010/0197028 A1  8/2010  Watkins et al.

FOREIGN PATENT DOCUMENTS

JP    2002-511143 A    4/2002
JP    2006-119036 A    5/2006
(Continued)

OTHER PUBLICATIONS

Lenz et al. (Journal of Proteome Research, 2007, 6:443-458) (Year: 2007).*

(Continued)

*Primary Examiner* — Jeremy C Flinders
(74) *Attorney, Agent, or Firm* — NK Patent Law

(57) ABSTRACT

Biomarkers relating to pancreatic Beta-cell function, pancreatic Beta-cell glucose sensitivity, insulin resistance, and/or pancreatic Beta-cell-related disorders are provided. Methods based on the same biomarkers are also provided.

5 Claims, 2 Drawing Sheets

(51) Int. Cl.
- A61K 31/661 (2006.01)
- A61K 31/685 (2006.01)
- G01N 33/68 (2006.01)

(56) References Cited

FOREIGN PATENT DOCUMENTS

| JP | 2010-537157 A | 12/2010 |
|---|---|---|
| WO | 2009-014639 A2 | 1/2009 |
| WO | 2010-005982 A2 | 1/2010 |
| WO | 2010/114897 | 10/2010 |

OTHER PUBLICATIONS

International Search Report for PCT/US2012/054640, dated Jan. 23, 2013.
Soga et al., Lysophosphatidylcholine enchances glucose-dependent insulin secretion via an orphan G-protein-coupled receptor, Journal Biochemical and Biophysical Research Communications 326 (2005) 744-751.
Chandler et al., Nasal Absorption in the Rat. III. Effect of Lysophospholipids on Insulin Absorption and Nasal Histology, Pharmaceutical Research, vol. II, No. 11, 1994 1623-1630.
Yamanaka et al., Clinical implication of plasma lysophosphatidylcholine in type 2 diabetics, Summary, Japanese Journal of Clinical Chemistry, vol. 36, Issue 1, 2007, p. 59.
Gall et al., α-Hydroxybutyrate is an Early Biomarker of Insulin Resistance and Glucose Intolerance in a Nondiabetic Population, PLOS ONE, vol. 5, Issue 5, May 28, 2010, pp. 1-11.
Supplementary European Search Report for EP Application No. 12831223.8 completed Jun. 10, 2015.
Cobb, J. et al., "A novel fasting blood test for insulin resistance and prediabetes", Journal of Diabetes Science and Technology, vol. 7, Issue 1, Jan. 2013, pp. 100-110.
Ferrannini E., et al., Early metabolic markers of the development of dysglycemia and type 2 diabetes and their physiological significance, Diabetes, vol. 62, Issue 5, May 2013, pp. 1730-1737.
Fiehn, O., et al., "Plasma metabolomic profiles reflective of glucose homeostasis in non-diabetic and type 2 diabetic obese African-American women", PLOS One, vol. 5, Issue 12, Dec. 10, 2010, pp. 1-10.
Salek, R.M., et al., "A metabolomics comparison of urinary changes in type-2 diabetes in mouse, rat and human", Physiol Genomics, vol. 29, Issue 2, Apr. 2007, pp. 99-108.
English translation of Office Action for JP Application No. 2014-530734, dated Jul. 7, 2016.
Ahrén et al., Importance of Quantifying Insulin Secretion in Relation to Insulin Sensitivity to Accurately Assess Beta Cell Function in Clinical Studies, European Journal of Endocrinology, vol. 150, 2004, pp. 97-104.
Bonora et al., Prevalence of Insulin Resistance in Metabolic Disorders, Diabetes, vol. 47, Oct. 1998, pp. 1643-1649.
Polonsky et al., Non-Insulin-Dependent Diabetes Mellitus—A Genetically Programmed Failure of the Beta Cell to Compensate for Insulin Resistance, The New England Journal of Medicine, vol. 334, No. 12, Mar. 21, 1996, pp. 777-783.
Kasuga, Insulin Resistance and Pancreatic β Cell Failure, The Journal of Clinical Investigation, vol. 116, No. 7, Jul. 2006, pp. 1756-1760.
Weyer et al., The Natural History of Insulin Secretory Dysfunction and Insulin Resistance in the Pathogenesis of Type 2 Diabetes Mellitus, The Journal of Clinical Investigation, vol. 104, No. 6, Sep. 1999, pp. 787-794.

* cited by examiner

METHOD OF ASSESSING PANCREATIC BETA-CELL FUNCTION

This application is a National Stage application of International Application No. PCT/US2012/054640, filed Sep. 11, 2012, which claims the benefit of U.S. Provisional Application No. 61/534,679, filed Sep. 14, 2011, the entire contents of which are hereby incorporated herein by reference.

FIELD

The invention generally relates to biomarkers related to pancreatic beta-cell function, type 2 diabetes and insulin resistance-related disorders and methods based on the same biomarkers.

BACKGROUND

Diabetes is classified as either type 1 (early onset) or type 2 (adult onset), with type 2 comprising 90-95% of the cases of diabetes. Diabetes is the final stage in a disease process that begins to affect individuals long before the diagnosis of diabetes is made. Type 2 diabetes develops over 10 to 20 years and results from an impaired ability to utilize glucose (glucose utilization, glucose uptake in peripheral tissues) due to impaired sensitivity to insulin (insulin resistance).

Moreover, insulin resistance is central to development of a number of different diseases and conditions, such as nonalcoholic steatohepatitis (NASH), polycystic ovary syndrome (PCOS), cardiovascular disease, metabolic syndrome, and hypertension.

In pre-diabetes, insulin becomes less effective at helping tissues metabolize glucose. Pre-diabetics may be detectable as early as 20 years before diabetic symptoms become evident. Studies have shown that although patients show very few overt symptoms, long-term physiological damage is already occurring at this stage. Up to 60% of these individuals will progress to type 2 diabetes within 10 years.

The American Diabetes Association (ADA) has recommended routine screening to detect patients with pre-diabetes. Current screening methods for pre-diabetes include the fasting plasma glucose (FPG) test, the oral glucose tolerance test (OGTT), the fasting insulin test and the hyperinsulinemic euglycemic clamp (HI clamp). The first two tests are used clinically whereas the latter two tests are used extensively in research but rarely in the clinic. In addition, mathematical means (e.g., HOMA, QUICKI) that consider the fasting glucose and insulin levels together have been proposed. However, normal plasma insulin concentrations vary considerably between individuals as well as within an individual throughout the day. Further, these methods suffer from variability and methodological differences between laboratories and do not correlate rigorously with HI clamp studies.

Worldwide, an estimated 194 million adults have type 2 diabetes and this number is expected to increase to 333 million by 2025, largely due to the epidemic of obesity in westernized societies. In the United States, it is estimated that over 54 million adults are pre-diabetic. There are approximately 1.5 million new cases of type 2 diabetes a year in the United States. The annual US healthcare cost for diabetes is estimated at $174 billion. This figure has risen more than 32% since 2002. In industrialized countries such as the U.S., about 25% of medical expenditures treat glycemic control, 50% is associated with general medical care associated with diabetes, and the remaining 25% of the costs go to treat long-term complications, primarily cardiovascular disease. Considering the distribution of the healthcare costs and the fact that insulin resistance is a direct causal factor in cardiovascular disease and diabetes progression, it is no surprise that cardiovascular disease accounts for 70-80% of the mortality observed for diabetic patients. Detecting and preventing type 2 diabetes has become a major health care priority.

Diabetes may also lead to the development of other diseases or conditions, or is a risk factor in the development of conditions such as Metabolic Syndrome and cardiovascular diseases. Metabolic Syndrome is the clustering of a set of risk factors in an individual. According to the American Heart Association these risk factors include: abdominal obesity, decreased ability to properly process glucose (insulin resistance or glucose intolerance), dyslipidemia (high triglycerides, high LDL, low HDL cholesterol), hypertension, prothrombotic state (high fibrinogen or plasminogen activator inhibitor-1 in the blood) and proinflammatory state (elevated C-reactive protein in the blood). Metabolic Syndrome is also known as syndrome X, insulin resistance syndrome, obesity syndrome, dysmetabolic syndrome and Reaven's syndrome. Patients diagnosed with Metabolic Syndrome are at an increased risk of developing diabetes, cardiac and vascular disease. It is estimated that, in the United States, 20% of the adults (>50 million people) have metabolic syndrome. While it can affect anyone at any age, the incidence increases with increasing age and in individuals who are inactive, and significantly overweight, especially with excess abdominal fat.

Type 2 diabetes is the most common form of diabetes in the United States. According to the American Diabetes Foundation over 90% of the US diabetics suffer from Type 2 diabetes. Individuals with Type 2 diabetes have a combination of increased insulin resistance and decreased insulin secretion that combine to cause hyperglycemia. Most persons with Type 2 diabetes have Metabolic Syndrome.

The diagnosis for Metabolic Syndrome is based upon the clustering of three or more of the risk factors in an individual. A variety of medical organizations have definitions for the Metabolic Syndrome. The criteria proposed by the National Cholesterol Education Program (NCEP) Adult Treatment Panel III (ATP III), with minor modifications, are currently recommended and widely used in the United States.

The American Heart Association and the National Heart, Lung, and Blood Institute recommend that the metabolic syndrome be identified as the presence of three or more of these components: increased waist circumference (Men—equal to or greater than 40 inches (102 cm), Women—equal to or greater than 35 inches (88 cm); elevated triglycerides (equal to or greater than 150 mg/dL); reduced HDL ("good") cholesterol (Men—less than 40 mg/dL, Women—less than 50 mg/dL); elevated blood pressure (equal to or greater than 130/85 mm Hg); elevated fasting glucose (equal to or greater than 100 mg/dL).

Type 2 diabetes develops slowly and often people first learn they have type 2 diabetes through blood tests done for another condition or as part of a routine exam. In some cases, type 2 diabetes may not be detected before damage to eyes, kidneys or other organs has occurred. A need exists for an objective, biochemical evaluation (e.g. lab test) that can be administered by a primary care provider to identify individuals that are at risk of developing Metabolic Syndrome or Type 2 diabetes.

Newer, more innovative molecular diagnostics that reflect the mechanisms of the patho-physiological progression, including assessing and monitoring functional beta-cell mass, to pre-diabetes and diabetes are needed because the prevalence of pre-diabetes and diabetes is increasing in global epidemic proportions. Mirroring the obesity epidemic, pre-diabetes and diabetes are largely preventable but are frequently undiagnosed or diagnosed too late due to the asymptomatic nature of the progression to clinical disease. As the disease progresses beta-cell function diminishes.

Although insulin resistance plays a central role in the development of numerous diseases, it is not readily detectable using many of the clinical measurements for pre-diabetic conditions. Insulin resistance develops prior to the onset of hyperglycemia and is associated with increased production of insulin. Over time (decades) the ability of the cell to respond to insulin decreases and the subject becomes resistant to the action of insulin (i.e., insulin resistant, IR). Eventually the beta-cells of the pancreas cannot produce sufficient insulin to compensate for the decreased insulin sensitivity and the beta-cells begin to lose function and apoptosis is triggered. Beta-cell function may be decreased as much as 80% in pre-diabetic subjects. As beta-cell dysfunction increases the production of insulin decreases resulting in lower insulin levels and high glucose levels in diabetic subjects. Vascular damage is associated with the increase in insulin resistance and the development of type 2 diabetes. The inability and, ultimately the failure, of pancreatic beta-cells to adapt the beta-cell mass (by activating beta-cell proliferation and differentiation, and inhibiting beta-cell apoptosis) to insulin demand eventually leads to a decrease in the functional beta-cell mass. Early detection of decreasing beta-cell function can facilitate earlier therapeutic intervention (drugs, lifestyle changes, etc) that will slow disease progression and, if intervention is sufficiently early, can restore functional beta-cell mass.

Current methods estimate the steady state beta-cell function as a percentage of a normal reference population. However, while the measures correspond well, they are not equivalent to non-steady state estimates of beta-cell function derived from stimulatory models such as the hyperinsulinaemic clamp, the hyperglycaemic clamp, the intravenous glucose tolerance test or the oral glucose tolerance test. Other methods have been developed using mathematical models to estimate beta cell function, such as the HOMA (Homeostasis Assessment Model). The equations, while widely used, are not appropriate for use with currently available insulin assays. Subsequently a quick and easy HOMA calculator was made available. While the HOMA calculator provides a quick and easy method for researchers wishing to use model-derived estimates of beta-cell function, it is still an indirect estimate that is insufficient to assess and monitor beta-cell function. Further, the development of therapeutic agents that facilitate the maintenance of functional beta-cell mass is needed to prevent and manage type 2 diabetes and related disorders.

Therefore there is an unmet need for diagnostic biomarkers and tests that can identify pancreatic beta-cell dysfunction and determine the risk of disease progression in subjects with impaired functional pancreatic beta-cell mass. Beta-cell function biomarkers and diagnostic tests can better identify and determine the risk of diabetes development in a pre-diabetic subject, can monitor disease development and progression and/or regression, can allow new therapeutic treatments to be developed and can be used to test therapeutic agents for efficacy on maintaining functional pancreatic beta-cell mass and thereby preventing or reversing type 2 diabetes and/or preventing related diseases. Further, a need exists for diagnostic biomarkers to more effectively assess the efficacy and safety of pre-diabetic and diabetic therapeutic candidates.

SUMMARY

In one embodiment, a method for assessing pancreatic beta-cell function in a subject is provided comprising: obtaining a biological sample from a subject; analyzing the biological sample from the subject to determine the level(s) of one or more biomarkers selected from the group consisting of 2-hydroxybutyrate (also referred to herein as α-hydroxybutyrate, α-OH-butyrate, alpha-hydroxybutyrate, AHB, 2-HB, α-HB), linoleoyl lysophosphatidylcholine (also referred to herein as linoleoylglycerophosphocholine, linoleoyl-lyso-GPC, linoleoyl-LPC, linoleoyl LPC, LGPC, L-GPC, L-LPC), decanoyl carnitine, octanoyl carnitine, 3-hydroxy-butyrate, 3-methyl-2-oxo-butyric acid, arginine, betaine, creatine, docosatetraenoic acid, glutamic acid, glycine, linoleic acid, linolenic acid, margaric acid, oleic acid, oleoyl lysophosphatidylcholine, palmitate, palmitoleic acid, palmitoyl lysophosphatidylcholine, serine, stearate, threonine, tryptophan, gamma-glutamyl-leucine, glutamyl-valine, stearoyl-lyso-GPC, 10-heptadecenoic acid, and 1,5-anhydroglucitol; and comparing the level(s) of the one or more biomarkers in the sample to functional pancreatic beta-cell reference levels of the one or more biomarkers in order to assess whether the subject has sufficient pancreatic beta-cell function. In an aspect of this invention, the one or more biomarkers are selected from the group consisting of 2-hydroxybutyrate and linoleoyl lysophosphatidylcholine. In this aspect, higher or elevated levels of 2-hydroxybutyrate compared to normal beta-cell levels indicate beta-cell dysfunction and lower or decreased levels of linoleoyl lysoglycerophospocholine compared to normal beta-cell levels indicate beta-cell dysfunction.

In yet another embodiment, a method of monitoring the progression or regression of pancreatic In another embodiment, a method of classifying a subject as having normal pancreatic beta-cell function or having compromised pancreatic beta-cell function is provided comprising: analyzing the biological sample from the subject to determine the level(s) of one or more biomarkers selected from the group consisting of 2-hydroxybutyrate, linoleoyl lysophosphatidylcholine, decanoyl carnitine, octanoyl carnitine, 3-hydroxy-butyrate, 3-methyl-2-oxo-butyric acid, arginine, betaine, creatine, docosatetraenoic acid, glutamic acid, glycine, linoleic acid, linolenic acid, margaric acid, oleic acid, oleoyl lysophosphatidylcholine, palmitate, palmitoleic acid, palmitoyl lysophosphatidylcholine, serine, stearate, threonine, tryptophan, gamma-glutamyl-leucine, glutamyl-valine, stearoyl-lyso-GPC, 10-heptadecenoic acid, and 1,5-anhydroglucitol; and comparing the level(s) of the one or more biomarkers in the sample to beta-cell function reference levels of the one or more biomarkers in order to classify the subject as having normal pancreatic beta-cell function or having compromised pancreatic beta-cell function. In an aspect of the invention, the one or more biomarkers are selected from the group consisting of 2-hydroxybutyrate and linoleoyl lysophosphatidylcholine. In this aspect, higher or elevated levels of 2-hydroxybutyrate compared to normal beta-cell levels indicate beta-cell dysfunction and lower or decreased levels of linoleoyl lysoglycerophosphocholine compared to normal beta-cell levels indicate compromised beta-cell function; and similar levels of 2-hydroxybutyrate compared to normal beta-cell levels indicate normal pancreatic beta-cell function and similar levels of linoleoyl lysoglycerophosphocholine compared to normal beta-cell levels indicate normal pancreatic beta-cell function.

In yet another embodiment, a method of monitoring the progression or regression of pancreatic beta-cell function in a subject is provided comprising: analyzing the biological sample from the subject to determine the level(s) of one or more biomarkers selected from the group consisting of 2-hydroxybutyrate, linoleoyl lysophosphatidylcholine, decanoyl carnitine, octanoyl carnitine, 3-hydroxy-butyrate, 3-methyl-2-oxo-butyric acid, arginine, betaine, creatine, docosatetraenoic acid, glutamic acid, glycine, linoleic acid, linolenic acid, margaric acid, oleic acid, oleoyl lysophosphatidylcholine, palmitate, palmitoleic acid, palmitoyl lysophosphatidylcholine, serine, stearate, threonine, tryptophan, gamma-glutamyl-leucine, glutamyl-valine, stearoyl-lyso-GPC, 10-heptadecenoic acid, and 1,5-anhydroglucitol; and comparing the level(s) of the one or more biomarkers in the sample to pancreatic beta-cell function progression and/or pancreatic beta-cell-regression reference levels of the one or more biomarkers in order to monitor the progression or regression of pancreatic beta-cell function in the subject. In an aspect of the invention, the one or more biomarkers are selected from the group consisting of 2-hydroxybutyrate and linoleoyl lysophosphatidylcholine.

In yet another embodiment, a method of monitoring the efficacy of insulin resistance treatment on pancreatic beta-cell function is provided, comprising: analyzing the biological sample from a subject to determine the level(s) of one or more biomarkers selected from the group consisting of 2-hydroxybutyrate, linoleoyl lysophosphatidylcholine, decanoyl carnitine, octanoyl carnitine, 3-hydroxy-butyrate, 3-methyl-2-oxo-butyric acid, arginine, betaine, creatine, docosatetraenoic acid, glutamic acid, glycine, linoleic acid, linolenic acid, margaric acid, oleic acid, oleoyl lysophosphatidylcholine, palmitate, palmitoleic acid, palmitoyl lysophosphatidylcholine, serine, stearate, threonine, tryptophan, gamma-glutamyl-leucine, glutamyl-valine, stearoyl-lyso-GPC, 10-heptadecenoic acid, and 1,5-anhydroglucitol; treating the subject for insulin resistance; analyzing a second biological sample from the subject to determine the level(s) of the one or more biomarkers, the second sample obtained from the subject at a second time point after treatment; and comparing the level(s) of one or more biomarkers in the first sample to the level(s) of the one or more biomarkers in the second sample to assess the efficacy of the treatment for treating insulin resistance on pancreatic beta-cell function.

In another embodiment, a method for determining a subject's probability of having compromised pancreatic beta-cell function is provided comprising: obtaining a biological sample from a subject; analyzing the biological sample from the subject to determine the level(s) of one or more biomarkers selected from the group consisting of 2-hydroxybutyrate, linoleoyl lysophosphatidylcholine, decanoyl carnitine, octanoyl carnitine, 3-hydroxy-butyrate, 3-methyl-2-oxo-butyric acid, arginine, betaine, creatine, docosatetraenoic acid, glutamic acid, glycine, linoleic acid, linolenic acid, margaric acid, oleic acid, oleoyl lysophosphatidylcholine, palmitate, palmitoleic acid, palmitoyl lysophosphatidylcholine, serine, stearate, threonine, tryptophan, gamma-glutamyl-leucine, glutamyl-valine, stearoyl-lyso-GPC, 10-heptadecenoic acid, and 1,5-anhydroglucitol, predicting the pancreatic beta-cell function in the subject by comparing the level(s) of the one or more biomarkers in the sample to pancreatic beta-cell reference levels of the one or more biomarkers; comparing the predicted pancreatic beta-cell function to an algorithm for pancreatic beta-cell function based on the one or more markers; and determining the probability that the subject has comprised pancreatic beta-cell function, thereby producing a pancreatic beta-cell function score.

In yet another embodiment, a method of identifying an agent capable of modulating the level of 2-hydroxybutyrate and/or linoleoyl glycerophosphocholine is provided comprising:analyzing a pancreatic beta-cell line from a subject at a first time point to determine the level(s) of one or more biomarkers selected from the group consisting of 2-hydroxy-butyrate, and linoleoyl lysophosphatidylcholine contacting the beta-cell line with a test agent; analyzing the cell line at a second time point to determine the level(s) of the one or more biomarkers, the second time point being a time after contacting with the test agent; and comparing the level(s) of one or more biomarkers in the cell line at the first time point to the level(s) of the one or more biomarkers in the cell line at the second time point to identify an agent capable of modulating the level of the one or more biomarkers.

In a further embodiment, a method for monitoring a subject's response to a course of treatment for insulin resistance is provided comprising: analyzing a first biological sample from a subject to determine the level(s) of one or more biomarkers selected from the group consisting of 2-hydroxybutyrate, linoleoyl lysophosphatidylcholine in the first sample obtained from the subject at a first time point; treating the subject for insulin resistance; analyzing a second biological sample from the subject to determine the level(s) of the one or more biomarkers, the second sample obtained from the subject at a second time point after treatment; using the determined levels of the level(s) of the one or more biomarkers and a reference model based on the one or more biomarkers to assess the efficacy of the treatment for treating insulin resistance.

In yet another embodiment, a method of identifying an agent capable of modulating functional beta-cell mass is provided comprising:analyzing a cell line from a subject at a first time point to determine the level(s) of one or more biomarkers selected from the group consisting of 2-hydroxy-butyrate, linoleoyl lysophosphatidylcholine, decanoyl carnitine, octanoyl carnitine, 3-hydroxy-butyrate, 3-methyl-2-oxo-butyric acid, arginine, betaine, creatine, docosatetraenoic acid, glutamic acid, glycine, linoleic acid, linolenic acid, margaric acid, oleic acid, oleoyl lysophosphatidylcholine, palmitate, palmitoleic acid, palmitoyl lysophosphatidylcholine, serine, stearate, threonine, tryptophan, gamma-glutamyl-leucine, glutamyl-valine, stearoyl-lyso-GPC, 10-heptadecenoic acid, and 1,5-anhydroglucitol and/or one or more biochemicals and/or metabolites in a pathway related to the one or more biomarkers; contacting the cell line with a test agent; analyzing the cell line at a second time point to determine the level(s) of the one or more biomarkers and/or one or more biochemicals and/or metabolites in a pathway related to the one or more biomarkers, the second time point being a time after contacting with the test agent; comparing the level(s) of one or more biomarkers and/or biochemicals and/or metabolites in the cell line at the first time point to the level(s) of the one or more biomarkers and/or biochemicals and/or metabolites in the cell line at the second time point to identify an agent capable of modulating functional beta-cell mass.

In a further embodiment, a method of treating subject having compromised beta-cell function is provided comprising: administering to the subject a therapeutic agent capable of modulating the level(s) of one or more biomarkers selected from the group consisting of 2-hydroxybutyrate, linoleoyl lysophosphatidylcholine, decanoyl carnitine, octanoyl carnitine, 3-hydroxy-butyrate, 3-methyl-2-oxo-butyric acid, arginine, betaine, creatine, docosatetraenoic acid, glutamic acid, glycine, linoleic acid, linolenic acid, margaric acid, oleic acid, oleoyl lysophosphatidylcholine, palmitate, palmitoleic acid, palmitoyl lysophosphatidylcholine, serine, stearate, threonine, tryptophan, gamma-glutamyl-leucine, glutamyl-valine, stearoyl-lyso-GPC, 10-heptadecenoic acid, and 1,5-anhydroglucitol, and/or one or more biochemicals and/or metabolites in a pathway related to the one or more biomarkers.

DETAILED DESCRIPTION

Figure 1:
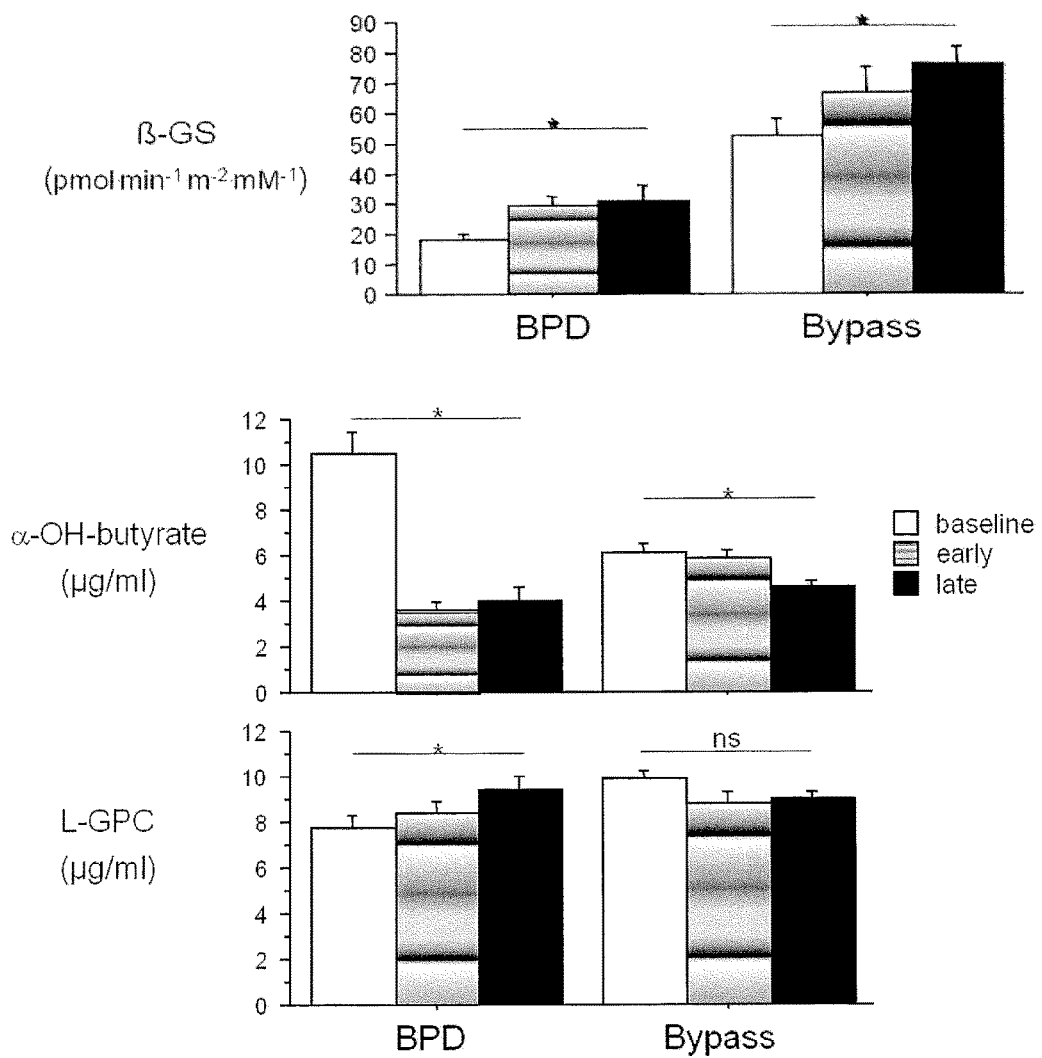
FIG. 1. Levels of biomarkers 2-FIB and L-GPC at baseline and at two timepoints following therapeutic surgery.

The present invention relates to biomarkers correlated to pancreatic beta-cell function; methods for diagnosis and/or aiding in the diagnosis of pancreatic beta-cell disorders; methods of monitoring progression/regression of pancreatic beta-cell function; methods of assessing efficacy of treatments and compositions for treating pancreatic beta-cell dysfunction; methods of screening compositions for activity in modulating biomarkers of pancreatic beta-cell function; methods of treating pancreatic beta-cell dysfunction; methods of identifying subjects for treatment with pancreatic beta-cell therapies; methods of identifying subjects for inclusion in clinical trials of pancreatic beta-cell therapies; as well as other methods based on biomarkers of pancreatic beta-cell function.

Current blood tests for assessing pancreatic beta-cell function perform poorly for evaluation of functional pancreatic beta-cell mass or involve significant medical procedures.

In one embodiment, metabolites that can be used in a simple body fluid (e.g., blood, urine, etc.) test to assess functional beta-cell mass are identified using metabolomic analysis. Such biomarkers correlate with pancreatic beta-cell function at a level similar to, or better than, the current method which is based on determining beta-cell glucose sensitivity using the oral glucose tolerance test (OGTT).

Independent studies were carried out to identify biomarker(s) that enable the early detection of changes in pancreatic beta-cell function in a subject. The biomarkers of the instant disclosure can be used to provide a score indicating the progression, regression or status of beta-cell dysfunction ("Beta-cell Score") in a subject. The score can be based upon a clinically significantly changed reference level for a biomarker and/or combination of biomarkers. The reference level can be derived from an algorithm or computed from indices for impaired beta-cell function and can be presented in a report. The Beta-cell Score places the subject in the range of pancreatic beta-cell function from normal (glucose sensitive) to impaired (glucose insensitive) and/or can be used to determine a probability that the subject has compromised pancreatic beta-cell function. Disease progression or remission can be monitored by periodic determination and monitoring of the Beta-cell Score. Response to therapeutic intervention can be determined by monitoring the Beta-cell Score. The Beta-cell Score can also be used to evaluate drug efficacy and/or to identify subjects to be treated with insulin resistance therapies, such as insulin sensitizers, or to identify subjects for inclusion in clinical trials.

Prior to describing this invention in further detail, however, the following terms will first be defined.

DEFINITIONS

"Biomarker" means a compound, preferably a metabolite, that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (e.g., a p-value less than 0.05 and/or a q-value of less than 0.10 as determined using either Welch's T-test or Wilcoxon's rank-sum Test). Alternatively, the biomarkers demonstrate a correlation with insulin resistance, or particular levels or stages of insulin resistance. The range of possible correlations is between negative (−) 1 and positive (+) 1. A result of negative (−) 1 means a perfect negative correlation and a positive (+) 1 means a perfect positive correlation, and 0 means no correlation at all. A "substantial positive correlation" refers to a biomarker having a correlation from +0.25 to +1.0 with a disorder or with a clinical measurement (e.g., M, Rd), while a "substantial negative correlation" refers to a correlation from −0.25 to −1.0 with a given disorder or clinical measurement. A "significant positive correlation" refers to a biomarker having a correlation of from +0.5 to +1.0 with a given disorder or clinical measurement (e.g., M, Rd), while a "significant negative correlation" refers to a correlation to a disorder of from −0.5 to −1.0 with a given disorder or clinical measurement.

The "level" of one or more biomarkers means the absolute or relative amount or concentration of the biomarker in the sample.

"Beta-cell", "β-cell" or "pancreatic beta-cell" refers to the insulin producing cell type located in the islets of Langerhans in the pancreas.

"Sample" or "biological sample" or "specimen" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, adipose tissue, aortic tissue, liver tissue, blood, blood plasma, saliva, serum, cerebrospinal fluid, cystic fluid, exudates, or urine.

"Subject" means any animal, but is preferably a mammal, such as, for example, a human, monkey, non-human primate, rat, mouse, cow, dog, cat, pig, horse, or rabbit.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "Beta-cell dysfunction-positive reference level" of a biomarker means a level of a biomarker that is indicative of a positive diagnosis of pancreatic beta-cell dysfunction in a subject, and a "Beta-cell dysfunction-negative reference level" of a biomarker means a level of a biomarker that is indicative of a negative diagnosis of compromised pancreatic beta-cell function in a subject (that is, the beta-cell function is normal or not compromised). As another example, a "Beta-cell dysfunction-progression-positive reference level" of a biomarker means a level of a biomarker that is indicative of progression of pancreatic beta-cell dysfunction (i.e., worsening of beta-cell dysfunction) in a subject, and a "Beta-cell dysfunction-regression-positive reference level" of a biomarker means a level of a biomarker that is indicative of regression of pancreatic beta-cell dysfunction (e.g., regeneration of functional beta-cell mass). A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. A "reference level" may also be a "standard curve reference level" based on the levels of one or more biomarkers determined from a population and plotted on appropriate axes to produce a reference curve (e.g. a standard probability curve). Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). A standard curve reference level may be determined from a group of reference levels from a group of subjects having a particular disease state, phenotype, or lack thereof (e.g. known glucose disposal rates) using statistical analysis, such as univariate or multivariate regression analysis, logistic regression analysis, linear regression analysis, and the like of the levels of such biomarkers in samples from the group. Such reference levels may also be tailored to specific techniques that are used to measure levels of biomarkers in biological samples (e.g., LC-MS, GC-MS, NMR, enzyme assays, etc.), where the levels of biomarkers may differ based on the specific technique that is used.

"Non-biomarker compound" means a compound that is not differentially present in a biological sample from a subject or a group of subjects having a first phenotype (e.g., having a first disease) as compared to a biological sample from a subject or group of subjects having a second phenotype (e.g., not having the first disease). Such non-biomarker compounds may, however, be biomarkers in a biological sample from a subject or a group of subjects having a third phenotype (e.g., having a second disease) as compared to the first phenotype (e.g., having the first disease) or the second phenotype (e.g., not having the first disease).

"Metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

"Metabolic profile", or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques.

"Metabolome" means all of the small molecules present in a given organism.

"Diabetes" refers to a group of metabolic diseases characterized by high blood sugar (glucose) levels which result from defects in insulin secretion or action, or both.

"Type 2 diabetes" refers to one of the two major types of diabetes, the type in which the beta cells of the pancreas produce insulin, at least in the early stages of the disease, but the body is unable to use it effectively because the cells of the body are resistant to the action of insulin. In later stages of the disease the beta cells may stop producing insulin. Type 2 diabetes is also known as insulin-resistant diabetes, non-insulin dependent diabetes and adult-onset diabetes.

"Pre-diabetes" refers to one or more early diabetes-related conditions including impaired glucose utilization, abnormal or impaired fasting glucose levels, impaired glucose tolerance, impaired insulin sensitivity and insulin resistance.

"Beta-cell dysfunction" or "beta-cell impairment" or "impaired beta-cell function" refers to a condition in which pancreatic beta-cells lose function and are unable to produce adequate quantities of insulin. Beta-cells store and release insulin and function to assist the liver in maintaining baseline glucose level by quickly releasing stored insulin while simultaneously producing more insulin in response to spikes in blood glucose.

"Glucose sensitivity" refers to the ability of beta-cells to respond to elevated blood glucose levels by releasing stored insulin and producing more insulin.

"Insulin resistant" refers to the condition when cells become resistant to the effects of insulin—a hormone that regulates the uptake of glucose into cells—or when the amount of insulin produced is insufficient to maintain a normal glucose level. Cells are diminished in the ability to respond to the action of insulin in promoting the transport of the sugar glucose from blood into muscles and other tissues (i.e. sensitivity to insulin decreases). Eventually, the pancreas produces far more insulin than normal and the cells continue to be resistant. As long as enough insulin is produced to overcome this resistance, blood glucose levels remain normal. Once the pancreas is no longer able to keep up, blood glucose starts to rise, resulting in diabetes. Insulin resistance ranges from normal (insulin sensitive) to insulin resistant (IR).

"Insulin sensitivity" refers to the ability of cells to respond to the effects of insulin to regulate the uptake and utilization of glucose. Insulin sensitivity ranges from normal (insulin sensitive) to Insulin Resistant (IR).

The "Pancreatic Beta-cell Score" or "β-cell Score" is a measure of the progression of compromised pancreatic beta-cell function in a subject based upon the predicted glucose sensitivity calculated using the pancreatic beta-cell biomarkers (e.g. along with models and/or algorithms) that will allow a physician to determine the probability that a subject has compromised pancreatic beta-cell function.

"Glucose utilization" refers to the absorption of glucose from the blood by muscle and fat cells and utilization of the sugar for cellular metabolism. The uptake of glucose into cells is stimulated by insulin.

"Rd" refers to glucose disposal rate (Rate of disappearance of glucose), a metric for glucose utilization. The rate at which glucose disappears from the blood (disposal rate) is an indication of the ability of the body to respond to insulin (i.e. insulin sensitive). There are several methods to determine Rd and the hyperinsulinemic euglycemic clamp is regarded as the "gold standard" method. In this technique, while a fixed amount of insulin is infused, the blood glucose is "clamped" at a predetermined level by the titration of a variable rate of glucose infusion. The underlying principle is that upon reaching steady state, by definition, glucose disposal is equivalent to glucose appearance. During hyperinsulinemia, glucose disposal (Rd) is primarily accounted for by glucose uptake into skeletal muscle, and glucose appearance is equal to the sum of the exogenous glucose infusion rate plus the rate of hepatic glucose output (HGO). The rate of glucose infusion during the last 30 minutes of the test determines insulin sensitivity. If high levels of glucose (Rd=7.5 mg/kg/min or higher) are required, the patient is insulin-sensitive. Very low levels (Rd=4.0 mg/kg/min or lower) of required glucose indicate that the body is resistant to insulin action. Levels between 4.0 and 7.5 mg/kg/min (Rd values between 4.0 mg/kg/min and 7.5 mg/kg/min) of required glucose are not definitive and suggest sensitivity to insulin is impaired and that the subject may have "impaired glucose tolerance," which may sometimes be a sign of insulin resistance.

"Mffm" and "Mwbm" refer to glucose disposal rate (M) calculated as the mean rate of glucose infusion during the past 60 minutes of the clamp examination (steady state) and expressed as milligrams per minute per kilogram of fat free mass (ffm) or whole body mass (wbm). Subjects with an Mffm less than 45 umol/min/kg ffm are generally regarded as insulin resistant. Subjects with an Mwbm of less than 5.6 mg/kg/min are generally regarded as insulin resistant.

"Dysglycemia" refers to disturbed blood sugar (i.e. glucose) regulation and results in abnormal blood glucose levels from any cause that contributes to disease. Subjects having higher than normal levels of blood sugar are considered "hyperglycemic" while subjects having lower than normal levels of blood sugar are considered "hypoglycemic".

"Impaired fasting glucose (IFG)" and "impaired glucose tolerance (IGT)" are the two clinical definitions of "pre-diabetes". IFG is defined as a fasting blood glucose concentration of 100-125 mg/dL. IGT is defined as a postprandial (after eating) blood glucose concentration of 140-199 mg/dL. It is known that IFG and IGT do not always detect the same pre-diabetic populations. Between the two populations there is approximately a 60% overlap observed. Fasting plasma glucose levels are a more efficient means of inferring a patient's pancreatic beta-cell function, or insulin secretion, whereas postprandial glucose levels are more frequently associated with inferring levels of insulin sensitivity or resistance. IGT is known to identify a greater percentage of the pre-diabetic population compared to IFG. The IFG condition is associated with lower insulin secretion, whereas the IGT condition is known to be strongly associated with insulin resistance. Numerous studies have been carried out that demonstrate that IGT individuals with normal FPG values are at increased risk for cardiovascular disease. Patients with normal FPG values may have abnormal postprandial glucose values and are often unaware of their risk for pre-diabetes, diabetes, and cardiovascular disease.

"Fasting plasma glucose (FPG) test" is a simple test measuring blood glucose levels after an 8 hour fast. According to the ADA, blood glucose concentration of 100-125 mg/dL is considered IFG and defines pre-diabetes whereas ≥126 mg/dL defines diabetes. As stated by the ADA, FPG is the preferred test to diagnose diabetes and pre-diabetes due to its ease of use, patient acceptability, lower cost, and relative reproducibility. The weakness in the FPG test is that patients are quite advanced toward Type 2 Diabetes before fasting glucose levels change.

"Oral glucose tolerance test (OGTT)", a dynamic measurement of glucose, is a postprandial measurement of a patient's blood glucose levels after oral ingestion of a 75 g glucose drink. Traditional measurements include a fasting blood sample at the beginning of the test, a one hour time point blood sample, and a 2 hour time point blood sample. A patient's blood glucose concentration at the 2 hour time point defines the level of glucose tolerance: Normal glucose tolerance (NGT)≤140 mg/dL blood glucose; Impaired glucose tolerance (IGT)=140-199 mg/dL blood glucose; Diabetes ≥200 mg/dL blood glucose. As stated by the ADA, even though the OGTT is known to be more sensitive and specific at diagnosing pre-diabetes and diabetes, it is not recommended for routine clinical use because of its poor reproducibility and difficulty to perform in practice. OGTT provides a measure of beta-cell glucose sensitivity.

"Fasting insulin test" measures the circulating mature form of insulin in plasma. The current definition of hyperinsulinemia is difficult due to lack of standardization of insulin immunoassays, cross-reactivity to proinsulin forms, and no consensus on analytical requirements for the assays. Within-assay CVs range from 3.7%-39% and among-assay CVs range from 12%-66%. Therefore, fasting insulin is not commonly measured in the clinical setting and is limited to the research setting.

The "hyperinsulinemic euglycemic clamp (HI clamp)" is considered worldwide as the "gold standard" for measuring insulin resistance in patients. It is performed in a research setting, requires insertion of two catheters into the patient and the patient must remain immobilized for up to six hours. The HI clamp involves creating steady-state hyperinsulinemia by insulin infusion, along with parallel glucose infusion in order to quantify the required amount of glucose to maintain euglycemia (normal concentration of glucose in the blood; also called normoglycemia). The result is a measure of the insulin-dependent glucose disposal rate (Rd), measuring the peripheral uptake of glucose by the muscle (primarily) and adipose tissues. This rate of glucose uptake is notated by M, whole body glucose metabolism by insulin action under steady state conditions. Therefore, a high M indicates high insulin sensitivity and a lower M value indicates reduced insulin sensitivity, i.e. insulin resistant. The HI clamp requires three trained professionals to carry out the procedure, including simultaneous infusions of insulin and glucose over 2-4 hours and frequent blood sampling every 5 minutes for analysis of insulin and glucose levels. Due to the high cost, complexity, and time required for the HI clamp, this procedure is strictly limited to the clinical research setting.

"Obesity" refers to a chronic condition defined by an excess amount body fat. The normal amount of body fat (expressed as percentage of body weight) is between 25-30% in women and 18-23% in men. Women with over 30% body fat and men with over 25% body fat are considered obese.

"Body Mass Index, (or BMI)" refers to a calculation that uses the height and weight of an individual to estimate the amount of the individual's body fat. Too much body fat (e.g. obesity) can lead to illnesses and other health problems. BMI is the measurement of choice for many physicians and researchers studying obesity. BMI is calculated using a mathematical formula that takes into account both height and weight of the individual. BMI equals a person's weight in kilograms divided by height in meters squared. (BMI=kg/m$^2$). Subjects having a BMI less than 19 are considered to be underweight, while those with a BMI of between 19 and 25 are considered to be of normal weight, while a BMI of between 25 to 29 is generally considered overweight, while individuals with a BMI of 30 or more are typically considered obese. Morbid obesity refers to a subject having a BMI of 40 or greater.

"Insulin resistance related disorders" refers to diseases, disorders or conditions that are associated with (e.g., co-morbid) or increased in prevalence in subjects that are insulin resistant. For example, atherosclerosis, coronary artery disease, myocardial infarction, myocardial ischemia, dysglycemia, hypertension, metabolic syndrome, polycystic ovary syndrome, neuropathy, nephropathy, chronic kidney disease, fatty liver disease and the like.

I. Biomarkers

The biomarkers described herein were discovered using metabolomic profiling techniques. Such metabolomic profiling techniques are described in more detail in the Examples set forth below as well as in U.S. Pat. Nos. 7,005,255 and 7,329,489 and 7,635,556, 7,682,783, 7,682,784, and 7,550,258, the entire contents of all of which are hereby incorporated herein by reference.

Generally, metabolic profiles may be determined for biological samples from human subjects diagnosed with a condition such as having compromised beta-cell function as well as from one or more other groups of human subjects (e.g., healthy control subjects with normal beta-cell function and normal glucose tolerance, subjects with impaired beta-cell function and impaired glucose tolerance, or subjects with insulin resistance, or subjects having type 2 diabetes). The metabolic profile for impaired beta-cell function may then be compared to the metabolic profile for biological samples from the one or more other groups of subjects. The comparisons may be conducted using models or algorithms, such as those described herein. Those molecules differentially present, including those molecules differentially present at a level that is statistically significant, in the metabolic profile of samples from subjects being insulin resistant or having a related disorder as compared to another group (e.g., healthy control subjects being insulin sensitive) may be identified as biomarkers to distinguish those groups.

In one embodiment, biomarkers for use in distinguishing or aiding in distinguishing, between subjects having impaired beta-cell function from subjects not having impaired beta-cell function include one or more of those listed Table 4. In another aspect, biomarkers for use in diagnosing or aiding in diagnosing a subject as being insulin resistant include one or more of those listed Table 4. In another example, biomarkers for use in categorizing, or aiding in categorizing, a subject as having impaired beta-cell function include one or more of those listed Table 4. In another example, biomarkers for use in identifying subjects for treatment by the administration of insulin resistance therapeutics or beta-cell function therapeutics include one or more of those listed in Table 4. In still another example, biomarkers for use in identifying subjects for admission into clinical trials for the administration of test compositions for effectiveness in treating beta-cell function or insulin resistance or related conditions, include one or more of those listed in Table 4.

Additional biomarkers for use in the methods disclosed herein include metabolites related to the biomarkers listed in Table 4. In addition, such additional biomarkers may also be useful in combination with the biomarkers in Table 4 for example as ratios of biomarkers and such additional biomarkers. Such metabolites may be related by proximity in a given pathway, or in a related pathway or associated with related pathways. Biochemical pathways related to one or more biomarkers listed in Table 4 include pathways involved in the formation of such biomarkers, pathways involved in the degradation of such biomarkers, and/or pathways in which the biomarkers are involved. For example, one biomarker listed in Table 4 is 2-hydroxybutyrate. Additional biomarkers for use in the methods of the present invention relating to 2-hydroxybutyrate include any of the enzymes, cofactors, genes, or the like involved in 2-hydroxybutyrate formation, metabolism, or utilization. For example, potential biomarkers from the 2-hydroxybutyrate formation pathway include, lactate dehydrogenase, hydroxybutyric acid dehydrogenase, alanine transaminase, gamma-cystathionase, branched-chain alpha-keto acid dehydrogenase, and the like. The substrates, intermediates, and enzymes in this pathway and related pathways may also be used as biomarkers for glucose disposal. For example, additional biomarkers related to 2-hydroxybutyrate include lactate dehydrogenase (LDH) or activation of hydroxybutyric acid dehydrogenase (HBDH) or branched chain alpha-keto acid dehydrogenase (BCKDH). In another embodiment, a pathway in which 2-hydroxybutyrate is involved is the citrate pathway (TCA pathway). When flux into the TCA cycle is reduced, there is typically an overflow of 2-hydroxybutyrate. Thus, any of the enzymes, co-factors, genes, and the like involved in the TCA cycle may also be biomarkers for glucose disposal, insulin resistance and related disorders. In addition, ratios of such enzymes, co-factors, genes and the like involved with such pathways with the biomarker linoleoyl-LPC, 3-hydroxybutyrate, 3-methyl-2-oxo-butyric acid, arginine, betaine, creatine, decanoyl carnitine, docosatetraenoic acid, glutamic acid, glycine, linoleic acid, linolenic acid, margaric acid, octanoyl carnitine, oleic acid, oleoyl-LPC, palmitate, palmitoleic acid, palmitoyl-LPC, serine, stearate, threonine, tryptophan, 1,5-anhydroglucitol, stearoyl-LPC, glutamyl valine, gamma-glutamyl-leucine, heptadecenoic acid, alpha-ketobutyrate, cysteine may also find use in the methods disclosed herein.

In addition, metabolites and pathways related to the biomarkers listed in Table 4 may be useful as sources of additional biomarkers for beta-cell function. For example, metabolites and pathways related to 2-hydroxybutyrate may also be biomarkers of beta-cell function, such as alpha-ketoacids, 3-methyl-2-oxobutyrate and 3-methyl-2-oxovalerate. Furthermore, other metabolites and agents involved in branched chain alpha-keto acid biosynthesis, metabolism, and utilization may also be useful as biomarkers of beta-cell function.

Any number of biomarkers may be used in the methods disclosed herein. That is, the disclosed methods may include the determination of the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, fifteen or more biomarkers, etc., including a combination of all of the biomarkers in Table 4. In another aspect, the number of biomarkers for use in the disclosed methods include the levels of about twenty-five or less biomarkers, twenty or less, fifteen or less, ten or less, nine or less, eight or less, seven or less, six or less, or five or less biomarkers. In another aspect, the number of biomarkers for use in the disclosed methods includes the levels of one, two, three, four, five, six, seven, eight, nine, ten, eleven, twelve, thirteen, fourteen, fifteen, twenty, or twenty-five biomarkers. Examples of specific combinations of biomarkers (and in some instances additional variables) that can be used in any of the methods disclosed herein are disclosed in the Examples (e.g., the models discussed in the Examples include specific combinations of biomarkers). In one example the biomarkers AHB and LGPC are used. The biomarkers may be used with or without the additional variables presented in the specific models.

The biomarkers disclosed herein may also be used to generate a beta-cell functional mass score ("β-cell Score") as a predictor or indicator of a subject's functional beta-cell mass or an indicator of the progression of beta-cell dysfunction on a spectrum ranging from no beta-cell dysfunction (normal cell function) to beta-cell apoptosis for use in any of the disclosed methods. Any method or algorithm can be used to generate a β-cell Score based on the biomarkers in Table 4 for use in the methods of the present disclosure.

The biomarkers, panels, and algorithms may provide sensitivity levels for detecting or predicting impaired beta-cell function greater than conventional methods, such as the oral glucose tolerance test, fasting plasma glucose test, hemoglobin A1C (and estimated average glucose, eAG), fasting plasma insulin, fasting proinsulin, adiponectin, HOMA-IR, and the like.

In other embodiments, the biomarkers, and algorithms disclosed herein may provide a specificity level for detecting or predicting impaired beta-cell function in a subject greater than conventional methods such as the oral glucose tolerance test, fasting plasma glucose test, adiponectin, and the like.

In addition, the methods disclosed herein using the biomarkers and models listed in the tables may be used in combination with clinical diagnostic measures of the respective conditions. Combinations with clinical diagnostics (such as oral glucose tolerance test, fasting plasma glucose test, free fatty acid measurement, hemoglobin A1C (and estimated average glucose, eAG) measurements, fasting plasma insulin measurements, fasting proinsulin measurements, fasting C-peptide measurements, glucose sensitivity (beta cell index) measurements, adiponectin measurements, uric acid measurements, systolic and diastolic blood pressure measurements, triglyceride measurements, triglyceride/HDL ratio, cholesterol (HDL, LDL) measurements, LDL/HDL ratio, waist/hip ratio, age, family history of diabetes (T1D and/or T2D), family history of cardiovascular disease) may facilitate the disclosed methods, or confirm results of the disclosed methods, (for example, facilitating or confirming diagnosis, monitoring progression or regression, and/or determining predisposition to pre-diabetes).

Any suitable method may be used to detect the biomarkers in a biological sample in order to determine the level(s) of the one or more biomarkers. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof (e.g. LC-MS-MS). Further, the level(s) of the one or more biomarkers may be detected indirectly, for example, by using an assay that measures the level of a compound (or compounds) that correlates with the level of the biomarker(s) that are desired to be measured.

In some embodiments, the biological samples for use in the detection of the biomarkers are transformed into analytical samples prior to the analysis of the level or detection of the biomarker in the sample. For example, in some embodiments, protein extractions may be performed to transform the sample prior to analysis by, for example, liquid chromatography (LC) or tandem mass spectrometry (MS-MS), or combinations thereof. In other embodiments, the samples may be transformed during the analysis, for example by tandem mass spectrometry methods.

II. Diagnostic Methods

The biomarkers described herein may be used to diagnose, or to aid in diagnosing, whether a subject has impaired beta-cell function. For example, biomarkers for use in diagnosing, or aiding in diagnosing, whether beta-cell function in a subject is impaired include one or more of those identified biomarkers Table 4. In one embodiment, the biomarkers include one or more of those identified in Table 4 and combinations thereof. Any biomarker listed in Table 4 may be used in the diagnostic methods, as well as any combination of the biomarkers listed in Table 4. In one embodiment the biomarkers include 2-hydroxybutyrate or linoleoyl LPC. In another example, the biomarkers include 2-hydroxybutyrate and/or linoleoyl LPC in combination with any other biomarker, such as, for example, 3-hydroxybutyrate, 3-methyl-2-oxo-butyric acid, arginine, betaine, creatine, docosatetraenoic acid, glutamic acid, glycine, linoleic acid, linolenic acid, margaric acid, oleic acid, oleoyl-LPC, palmitate, palmitoleic acid, palmitoyl-LPC, serine, stearate, threonine, tryptophan, 1,5-anhydroglucitol, stearoyl-LPC, glutamyl valine, gamma-glutamyl-leucine, heptadecenoic acid, alpha-ketobutyrate, cysteine, or combinations thereof.

Methods for diagnosing, or aiding in diagnosing, whether a subject has a disease or condition, such as having impaired beta-cell function, may be performed using one or more of the biomarkers identified in Table 4. A method of diagnosing (or aiding in diagnosing) whether a subject has a disease or condition, such as having impaired beta-cell function, comprises (1) analyzing a biological sample from a subject to determine the level(s) of one or more biomarkers of beta-cell function listed in Table 4 in the sample and (2) comparing the level(s) of the one or more biomarkers in the sample to beta-cell dysfunction-positive and/or beta-cell dysfunction-negative reference levels of the one or more biomarkers in order to diagnose (or aid in the diagnosis of) whether the subject is beta-cell function impaired. When such a method is used in aiding in the diagnosis of a disease or condition, such as impaired beta-cell function, the results of the method may be used along with other methods (or the results thereof) useful in the clinical determination of whether a subject has a given disease or condition. Methods useful in the clinical determination of whether a subject has a disease or condition such as impaired beta-cell function are known in the art. For example, methods useful in the clinical determination of whether a subject is beta-cell function impaired or is at risk of being beta-cell function impaired include, for example, the determination of glucose disposal rates (Rd, M-wbm, M-ffm), body weight measurements, waist circumference measurements, BMI determinations, waist/hip ratio, triglycerides measurements, cholesterol (HDL, LDL) measurements, LDL/HDL ratio, triglyceride/HDL ratio, age, family history of diabetes (T1D and/or T2D), family history of cardiovascular disease, Peptide YY measurements, C-peptide measurements, Hemoglobin A1C measurements and estimated average glucose, (eAG), adiponectin measurements, fasting plasma glucose measurements (e.g., oral glucose tolerance test, fasting plasma glucose test), free fatty acid measurements, fasting plasma insulin and pro-insulin measurements, systolic and diastolic blood pressure measurements, urate measurements and the like. Methods useful for the clinical determination of whether a subject has impaired beta-cell function include the hyperinsulinemic euglycemic clamp (HI clamp).

Independent studies were carried out to identify a set of biomarkers that when used with a polynomic algorithm enables the early detection of changes in beta-cell function in a subject. In one aspect, the biomarkers provided herein can be used to provide a physician with a β-cell Score indicating the progression of beta-cell function impairment in a subject. The score is based upon clinically significantly changed reference level(s) for a biomarker and/or combination of biomarkers. The reference level can be derived from an algorithm or computed from indices for impaired beta-cell glucose sensitivity. The β-cell Score places the subject in the range of beta-cell function from normal (i.e. glucose sensitive beta-cells) to compromised beta-cell function to highly compromised/impaired beta-cell function. The β-cell Score can be used in multiple ways: for example, beta-cell dysfunction progression or regression can be monitored by periodic determination and monitoring of the β-cell Score; response to therapeutic intervention can be determined by monitoring the β-cell Score; and drug efficacy can be evaluated using the β-cell Score.

Thus, the disclosure also provides methods for determining a subject's β-cell Score that may be performed using one or more of the biomarkers identified in Table 4 in the sample, and (2) comparing the level(s) of the one or more biomarkers of beta-cell dysfunction in the sample to beta-cell dysfunction reference levels of the one or more biomarkers in order to determine the subject's β-cell Score. Exemplary markers from Table 4 include 2-hydroxybutyrate and linoleoyl glycerophosphocholine (L-LPC, LGPC). The method may employ any number of markers selected from those listed in Table 4 including 1, 2, 3, 4, 5, 6, 7, 8, 9, 10, or more markers. Multiple biomarkers may be correlated with a given condition, such as having impaired beta-cell function or being insulin resistant, by any method, including statistical methods such as regression analysis.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

After the level(s) of the one or more biomarker(s) is determined, the level(s) may be compared to beta-cell dysfunction reference level(s) or reference curves of the one or more biomarker(s) to determine a rating for each of the one or more biomarker(s) in the sample. The rating(s) may be aggregated using any algorithm to create β-cell score for the subject. The algorithm may take into account any factors relating to the disease or condition, such as having β-cell function impairment, including the number of biomarkers, the correlation of the biomarkers to the disease or condition, etc.

In one example, the subject's predicted functional beta-cell level may be used to determine the probability that the subject is beta-cell function impaired (i.e. determine the subject's β-cell Score). For example, using a standardized curve generated using one or more biomarkers listed in Table 4, a subject predicted to have a beta-cell function level of 9, may have a 10% probability of being beta-cell function impaired. Alternatively, in another example, a subject predicted to have a beta-cell function level of 3 may have a 90% probability of being beta-cell function impaired.

The levels of one or more of the biomarkers of Table 4 may be determined in the methods of diagnosing and methods of aiding in diagnosing whether a subject has β-cell function impairment. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers in Table 4 and combinations thereof or any fraction thereof, may be determined and used in such methods. Determining levels of combinations of the biomarkers may allow greater sensitivity and specificity in diagnosing β-cell function impairment and aiding in the diagnosis of β-cell function impairment. For example, ratios of the levels of certain biomarkers (and non-biomarker compounds) in biological samples may allow greater sensitivity and specificity in diagnosing β-cell function impairment and aiding in the diagnosis of β-cell function impairment.

After the level(s) of the one or more biomarkers in the sample are determined, the level(s) are compared to beta-cell dysfunction-positive and/or beta-cell dysfunction—negative reference levels to aid in diagnosing or to diagnose whether the subject has β-cell function impairment. Levels of the one or more biomarkers in a sample matching the beta-cell dysfunction—positive reference levels (e.g., levels that are the same as the reference levels, substantially the same as the reference levels, above and/or below the minimum and/or maximum of the reference levels, and/or within the range of the reference levels) are indicative of a diagnosis of β-cell function impairment in the subject. Levels of the one or more biomarkers in a sample matching the pancreatic beta-cell dysfunction—negative reference levels (e.g., levels that are the same as the reference levels, substantially the same as the reference levels, above and/or below the minimum and/or maximum of the reference levels, and/or within the range of the reference levels) are indicative of a diagnosis of no β-cell function impairment in the subject. In addition, levels of the one or more biomarkers that are differentially present (especially at a level that is statistically significant) in the sample as compared to beta-cell dysfunction-negative reference levels are indicative of a diagnosis of β-cell function=impairment in the subject. Levels of the one or more biomarkers that are differentially present (especially at a level that is statistically significant) in the sample as compared to beta-cell dysfunction-positive reference levels are indicative of a diagnosis of no β-cell function impairment in the subject.

The level(s) of the one or more biomarkers may be compared to beta-cell dysfunction-positive and/or beta-cell dysfunction-negative reference levels using various techniques, including a simple comparison (e.g., a manual comparison) of the level(s) of the one or more biomarkers in the biological sample to beta-cell dysfunction-positive and/or beta-cell dysfunction-negative reference levels. The level(s) of the one or more biomarkers in the biological sample may also be compared to beta-cell dysfunction-positive and/or beta-cell dysfunction-negative reference levels using one or more statistical analyses (e.g., T-score, Z-score) or using a mathematical model (e.g., algorithm).

III. Monitoring Beta-Cell Function Impairment Progression/Regression

The identification of biomarkers herein allows for monitoring progression/regression of beta-cell function impairment or related conditions in a subject. A method of monitoring the progression/regression of beta-cell function impairment or related condition in a subject comprises (1) analyzing a first biological sample from a subject to determine the level(s) of one or more biomarkers for beta-cell function listed in Table 4, and combinations thereof, in the first sample obtained from the subject at a first time point, (2) analyzing a second biological sample from a subject to determine the level(s) of the one or more biomarkers, the second sample obtained from the subject at a second time point, and (3) comparing the level(s) of one or more biomarkers in the first sample to the level(s) of the one or more biomarkers in the second sample in order to monitor the progression/regression of the disease or condition in the subject. The results of the method are indicative of the course of beta-cell function impairment (i.e., progression (worsening function, decreased functional mass) or regression (improving function, increasing functional mass), if any change) in the subject. The change (if any) in the level(s) of the one or more biomarkers over time may be indicative of progression or regression of beta-cell function impairment in the subject. In order to characterize the course of beta-cell function impairment in the subject, the level(s) of the one or more biomarkers in the first sample, the level(s) of the one or more biomarkers in the second sample, and/or the results of the comparison of the levels of the biomarkers in the first and second samples may be compared to beta-cell dysfunction-positive and beta-cell dysfunction-negative reference levels. If the comparisons indicate that the level(s) of the one or more biomarkers are increasing or decreasing over time (e.g., in the second sample as compared to the first sample) to become more similar to the beta-cell dysfunction-positive reference levels (or less similar to the beta-cell dysfunction-negative reference levels), then the results are indicative of β-cell dysfunction progression. If the comparisons indicate that the level(s) of the one or more biomarkers are increasing or decreasing over time to become more similar to the beta-cell dysfunction-negative reference levels (or less similar to the beta-cell dysfunction-positive reference levels), then the results are indicative of β-cell dysfunction regression.

In one embodiment, the results of the method may be based on a β-cell Score which is representative of the probability of beta-cell function impairment in the subject and which can be monitored over time. By comparing the β-cell Score from a first time point sample to the β-cell Score from at least a second time point sample the progression or regression of beta-cell function can be determined. Such a method of monitoring the progression/regression of impaired beta-cell function in a subject comprises (1) analyzing a first biological sample from a subject to determine a β-cell score for the first sample obtained from the subject at a first time point, (2) analyzing a second biological sample from a subject to determine a second β-cell score, the second sample obtained from the subject at a second time point, and (3) comparing the β-cell score in the first sample to the β-cell score in the second sample in order to monitor the progression/regression of impaired beta-cell function in the subject. An increase in the probability of impaired beta-cell function from the first to the second time point is indicative of the progression of impaired beta-cell function in the subject, while a decrease in the probability from the first to the second time points is indicative of the regression of impaired beta-cell function in the subject.

Using the biomarkers and algorithm of the instant invention for progression monitoring may guide, or assist a physician's decision to implement preventative measures such as dietary restrictions, exercise, and/or early-stage drug treatment.

IV. Monitoring Therapeutic Efficacy:

The biomarkers provided also allow for the assessment of the efficacy of a composition for treating impaired beta-cell function. For example, the identification of biomarkers for beta-cell function also allows for assessment of the efficacy of a composition for treating impaired beta-cell function as well as the assessment of the relative efficacy of two or more compositions for treating beta-cell function impairment. Such assessments may be used, for example, in efficacy studies as well as in lead selection of compositions for treating the disease or condition. In addition, such assessments may be used to monitor the efficacy of surgical procedures and/or lifestyle interventions on insulin resistance in a subject. Surgical procedures include bariatric surgery, while lifestyle interventions include diet modification or reduction, exercise programs, and the like.

Thus, in one such embodiment, provided are methods of assessing the efficacy of a composition for treating a disease or condition such as impaired beta-cell function, or related condition comprising (1) analyzing, from a subject (or group of subjects) having a disease or condition such as impaired beta-cell function, or related condition and currently or previously being treated with a composition, a biological sample (or group of samples) to determine the level(s) of one or more biomarkers for beta-cell function selected from the biomarkers listed in Table 4, and (2) comparing the level(s) of the one or more biomarkers in the sample to (a) level(s) of the one or more biomarkers in a previously-taken biological sample from the subject, wherein the previously-taken biological sample was obtained from the subject before being treated with the composition, (b) beta-cell dysfunction-positive reference levels of the one or more biomarkers, (c) beta-cell dysfunction-negative reference levels of the one or more biomarkers, (d) beta-cell dysfunction-progression-positive reference levels of the one or more biomarkers, and/or (e) beta-cell dysfunction-regression-positive reference levels of the one or more biomarkers. The results of the comparison are indicative of the efficacy of the composition for treating the respective disease or condition.

In another embodiment, methods of assessing the efficacy of a surgical procedure for treating a disease or condition such as impaired beta-cell function, or related condition comprising (1) analyzing, from a subject (or group of subjects) having impaired beta-cell function, or related condition, and having previously undergone a surgical procedure, a biological sample (or group of samples) to determine the level(s) of one or more biomarkers for beta-cell function selected from the biomarkers listed in Table 4, and (2) comparing the level(s) of the one or more biomarkers in the sample to (a) level(s) of the one or more biomarkers in a previously-taken biological sample from the subject, wherein the previously-taken biological sample was obtained from the subject before undergoing the surgical procedure or taken immediately after undergoing the surgical procedure, (b) beta-cell dysfunction-positive reference levels of the one or more biomarkers, (c) beta-cell dysfunction-negative reference levels of the one or more biomarkers, (d) beta-cell dysfunction-progression-positive reference levels of the one or more biomarkers, and/or (e) beta-cell dysfunction-regression-positive reference levels of the one or more biomarkers. The results of the comparison are indicative of the efficacy of the surgical procedure for treating the respective disease or condition. In one embodiment, the surgical procedure is a gastro-intestinal surgical procedure, such as bariatric surgery.

The change (if any) in the level(s) of the one or more biomarkers over time may be indicative of progression or regression of beta-cell dysfunction in the subject. To characterize the course of a given disease or condition in the subject, the level(s) of the one or more biomarkers in the first sample, the level(s) of the one or more biomarkers in the second sample, and/or the results of the comparison of the levels of the biomarkers in the first and second samples may be compared to the respective disease- or condition-positive and/or disease- or condition-negative reference levels of the one or more biomarkers. If the comparisons indicate that the level(s) of the one or more biomarkers are increasing or decreasing over time (e.g., in the second sample as compared to the first sample) to become more similar to the disease- or condition-positive reference levels (or less similar to the disease- or condition-negative reference levels), then the results are indicative of the disease's or condition's progression. If the comparisons indicate that the level(s) of the one or more biomarkers are increasing or decreasing over time to become more similar to the disease- or condition-negative reference levels (or less similar to the disease- or condition-positive reference levels), then the results are indicative of the disease's or condition's regression.

For example, in order to characterize the course of beta-cell dysfunction in the subject, the level(s) of the one or more biomarkers in the first sample, the level(s) of the one or more biomarkers in the second sample, and/or the results of the comparison of the levels of the biomarkers in the first and second samples may be compared to beta-cell dysfunction-positive and/or beta-cell dysfunction-negative reference levels of the one or more biomarkers. If the comparisons indicate that the level(s) of the one or more biomarkers are increasing or decreasing over time (e.g., in the second sample as compared to the first sample) to become more similar to the beta-cell dysfunction-positive reference levels (or less similar to the beta-cell dysfunction-negative reference levels), then the results are indicative of beta-cell dysfunction progression (i.e., worsening beta-cell function). If the comparisons indicate that the level(s) of the one or more biomarkers are increasing or decreasing over time to become more similar to the beta-cell dysfunction-negative reference levels (or less similar to the beta-cell-dysfunction-positive reference levels), then the results are indicative of beta-cell dysfunction regression (i.e., improving beta-cell function).

The second sample may be obtained from the subject any period of time after the first sample is obtained. In one aspect, the second sample is obtained 1, 2, 3, 4, 5, 6, or more days after the first sample or after the initiation of the administration of a composition, surgical procedure, or lifestyle intervention. In another aspect, the second sample is obtained 1, 2, 3, 4, 5, 6, 7, 8, 9, 10, or more weeks after the first sample or after the initiation of the administration of a composition, surgical procedure, or lifestyle intervention. In another aspect, the second sample may be obtained 1, 2, 3, 4, 5, 6, 7, 8, 9, 10, 11, 12, or more months after the first sample or after the initiation of the administration of a composition, surgical procedure, or lifestyle intervention.

The course of a disease or condition such as beta-cell dysfunction in a subject may also be characterized by comparing the level(s) of the one or more biomarkers in the first sample, the level(s) of the one or more biomarkers in the second sample, and/or the results of the comparison of the levels of the biomarkers in the first and second samples to disease- or condition-progression-positive and/or disease- or condition-regression-positive reference levels. If the comparisons indicate that the level(s) of the one or more biomarkers are increasing or decreasing over time (e.g., in the second sample as compared to the first sample) to become more similar to the disease- or condition-progression-positive reference levels (or less similar to the disease- or condition-regression-positive reference levels), then the results are indicative of the disease or condition progression. If the comparisons indicate that the level(s) of the one or more biomarkers are increasing or decreasing over time to become more similar to the disease- or condition-regression-positive reference levels (or less similar to the disease- or condition-progression-positive reference levels), then the results are indicative of disease or condition regression.

As with the other methods described herein, the comparisons made in the methods of monitoring progression/regression of a disease or condition such as beta-cell dysfunction in a subject may be carried out using various techniques, including simple comparisons, one or more statistical analyses, and combinations thereof.

The results of the method may be used along with other methods (or the results thereof) useful in the clinical monitoring of progression/regression of the disease or condition in a subject.

As described above in connection with methods of diagnosing (or aiding in the diagnosis of) a disease or condition such as beta-cell dysfunction, any suitable method may be used to analyze the biological samples in order to determine the level(s) of the one or more biomarkers in the samples. In addition, the level(s) one or more biomarkers, including a combination of all of the biomarkers in Table 4 or any fraction thereof, may be determined and used in methods of monitoring progression/regression of the respective disease or condition in a subject.

V. Methods of Screening a Composition for Activity in Modulating Biomarkers

The biomarkers provided herein also allow for the screening of compositions for activity in modulating biomarkers associated with a disease or condition, such as beta-cell function impairment, which may be useful in treating the disease or condition. An exemplary method comprises assaying test compounds for activity in modulating the levels of one or more biomarkers listed in Table 4. The screening assays may be conducted in vitro (e.g., beta-cell assays), and/or in vivo, and may be in any form known in the art useful for assaying modulation of such biomarkers in the presence of a test composition. Exemplary assay methods include, for example, cell culture assays, organ culture assays, and in vivo assays (e.g., assay involving animal models). Another exemplary method comprises assaying test compounds for activity in modulating the levels of 2-hydroxybutyrate or linoleoyl-LPC.

For example, with regard to this method, the identification of biomarkers for beta-cell function also enables the screening of compositions for activity in modulating the identified biomarkers associated with beta-cell function, which may be useful in treating beta-cell impairment.

The methods for screening a composition for activity in modulating one or more biomarkers of a disease or condition such as impaired beta-cell function, or related disorder comprise (1) contacting one or more cells with a composition, (2) analyzing at least a portion of the one or more cells or a biological sample associated with the cells to determine the level(s) of one or more biomarkers of a disease or condition selected from the biomarkers provided in Table 4; and (3) comparing the level(s) of the one or more biomarkers with predetermined standard levels for the one or more biomarkers to determine whether the composition modulated the level(s) of the one or more biomarkers. In one embodiment, a method for screening a composition for activity in modulating one or more biomarkers of beta-cell function comprises (1) contacting one or more cells with a composition, (2) analyzing at least a portion of the one or more cells or a biological sample associated with the cells to determine the level(s) of one or more biomarkers of beta-cell function selected from the biomarkers listed in Table 4; and (3) comparing the level(s) of the one or more biomarkers with predetermined standard levels for the one or more biomarkers to determine whether the composition modulated the level(s) of the one or more biomarkers. The one or more biomarkers may be selected from the group consisting of AHB and L-LPC. As discussed above, the cells may be contacted with the composition in vitro and/or in vivo. The predetermined standard levels for the one or more biomarkers may be the levels of the one or more biomarkers in the one or more cells in the absence of the composition. The predetermined standard levels for the one or more biomarkers may also be the level(s) of the one or more biomarkers in control cells not contacted with the composition.

In addition, the methods may further comprise analyzing at least a portion of the one or more cells or a biological sample associated with the cells to determine the level(s) of one or more non-biomarker compounds of a disease or condition such as impaired beta-cell function. The levels of the non-biomarker compounds may then be compared to predetermined standard levels of the one or more non-biomarker compounds.

Any suitable method may be used to analyze at least a portion of the one or more cells or a biological sample associated with the cells in order to determine the level(s) of the one or more biomarkers (or levels of non-biomarker compounds). Suitable methods include chromatography (e.g., HPLC, gas chromatography, liquid chromatography), mass spectrometry (e.g., MS, MS-MS), ELISA, antibody linkage, other immunochemical techniques, biochemical or enzymatic reactions or assays, and combinations thereof.

Further, the level(s) of the one or more biomarkers (or levels of non-biomarker compounds) may be measured indirectly, for example, by using an assay that measures the level of a compound (or compounds) that correlates with the level of the biomarker(s) (or non-biomarker compounds) that are desired to be measured.

VI. Methods of Treatment

In another aspect, methods for treating a disease or condition such as beta-cell dysfunction are provided. The methods generally involve treating a subject having a disease or condition such as beta-cell dysfunction with an effective amount of L-LPC, or one or more biomarker(s) that are lowered in a subject having the disease or condition as compared to a healthy subject not having the disease or condition. The biomarkers that may be administered may comprise L-LPC, or L-LPC and one or more of the biomarkers Table 4 that are decreased in a disease or condition state as compared to subjects not having that disease or condition. Such biomarkers could be isolated based on the identity of the biomarker compound (i.e. compound name).

VII. Other Methods

Other methods of using the biomarkers discussed herein are also contemplated. For example, the methods described in U.S. Pat. Nos. 7,005,255; 7,329,489; 7,550,258; 7,550,260; 7,553,616; 7,635,556; 7,682,782; and 7,682,784 may be conducted using a small molecule profile comprising one or more of the biomarkers disclosed herein.

EXAMPLES

I. General Methods

A. Identification of Metabolic Profiles

Each sample was analyzed to determine the concentration of several hundred metabolites. Analytical techniques such as GC-MS (gas chromatography-mass spectrometry) and LC-MS (liquid chromatography-mass spectrometry) were used to analyze the metabolites. Multiple aliquots were simultaneously, and in parallel, analyzed, and, after appropriate quality control (QC), the information derived from each analysis was recombined. Every sample was characterized according to several thousand characteristics, which ultimately amount to several hundred chemical species. The techniques used were able to identify novel and chemically unnamed compounds.

B. Statistical Analysis:

The data was analyzed using several statistical methods to identify molecules (either known, named metabolites or unnamed metabolites) present at differential levels in a definable population or subpopulation (e.g., biomarkers for insulin resistant biological samples compared to control biological samples or compared to insulin sensitive patients) useful for distinguishing between the definable populations (e.g., insulin resistance and control, insulin resistance and insulin sensitive, insulin resistance and type-2 diabetes). Other molecules (either known, named metabolites or unnamed metabolites) in the definable population or subpopulation were also identified.

Random forest analyses were used for classification of samples into groups (e.g. disease or healthy, insulin resistant or normal insulin sensitivity). Random forests give an estimate of how well we can classify individuals in a new data set into each group, in contrast to a t-test, which tests whether the unknown means for two populations are different or not. Random forests create a set of classification trees based on continual sampling of the experimental units and compounds. Then each observation is classified based on the majority votes from all the classification trees.

Regression analysis was performed using the Random Forest Regression method and the Univariate Correlation/Linear Regression method to build models that are useful to identify the biomarker compounds that are associated with disease or disease indicators (e.g. Rd) and then to identify biomarker compounds useful to classify individuals according to for example, the level of glucose utilization as normal, insulin impaired, or insulin resistant. Biomarker compounds that are useful to predict disease or measures of disease (e.g. Rd) and that are positively or negatively correlated with disease or measures of disease (e.g. Rd) were identified in these analyses. All of the biomarker compounds identified in these analyses were statistically significant (p<0.05, q<0.1).

Recursive partitioning relates a 'dependent' variable (Y) to a collection of independent ('predictor') variables (X) in order to uncover—or simply understand—the elusive relationship, Y=f(X). The analysis was performed with the JMP program (SAS) to generate a decision tree. The statistical significance of the "split" of the data can be placed on a more quantitative footing by computing p-values, which discern the quality of a split relative to a random event. The significance level of each "split" of data into the nodes or branches of the tree was computed as p-values, which discern the quality of the split relative to a random event. It was given as LogWorth, which is the negative log 10 of a raw p-value.

Statistical analyses were performed with the program "R" available on the worldwide web at the website cran.r-project.org and in JMP 6.0.2 (SAS® Institute, Cary, N.C.).

Example 2

Identification of Biomarkers of Beta-Cell Function

Beta-cell function is highest in subjects having normal glucose tolerance (NGT), lower (i.e., impaired) in subjects having impaired glucose tolerance (IGT) and lowest in subjects having type 2 diabetes (T2D). Biomarkers of beta-cell function were identified from analysis of plasma samples from NGT, IGT and T2D subjects. Subjects were selected from participants in one of two study groups. The first group of subjects (Group 1) was selected from a prospective, observational cohort (Hills et al. Diabetologia (2004)) recruited at 19 centers in 13 countries in Europe, according to following inclusion criteria: either sex, age 30-60 years, clinically healthy, stratified by sex and by age according to 10-year age groups. Initial exclusion criteria were: treatment for obesity, hypertension, lipid disorders or diabetes, pregnancy, cardiovascular or chronic lung disease, weight change of ≥5 kg in last month, cancer (in last 5 years), and renal failure. Exclusion criteria after screening were: arterial blood pressure ≥140/90 mmHg, fasting plasma glucose >7.0 mmol/l, 2-hour plasma glucose (on a standard 75-g oral glucose tolerance test [OGTT]) ≥11.0 mmol/l, total serum cholesterol ≥7.8 mmol/l, serum triglycerides ≥4.6 mmol/l, and ECG abnormalities. Baseline examinations of these Group 1 subjects began in 2002 and were completed in 2005. Three year follow-up examinations began in 2005 and ended in 2008.

The second group of subjects (Group 2) was selected from the Prospective Study (family history T2D cohort). Baseline examinations of Group 2 subjects began in 1990 and routine follow-up examinations currently continue.

OGTT measurements were performed on both Group 1 and Group 2 participants at baseline and at three year follow-up. For Group 1, 1050 participants had OGTT measurements at both baseline and 3 years. For Group 2, 2585 participants had OGTT at both baseline and 3 years. Based on the OGTT measurement at follow-up, Group 1 and Group 2 subjects were categorized as stable NGT, i.e., fasting plasma glucose <5.6 mmol/l and 2-hour glucose <7.8 mmol/l) at baseline and follow-up, impaired glucose regulation (IGR comprising both impaired glucose tolerance (IGT, i.e., 2-hour glucose between 7.8-11.1 mmol/l), and impaired fasting glycemia (IFG, i.e., fasting glucose between 5.6-7.0 mmol/l), versus the subjects that progressed (i.e., "progressors") to dysglycemia (IGR based on aforementioned FPG and 2-hour glucose measurement ranges for IFG and IGT), or T2D (if fasting plasma glucose >7.0 mmol/l and 2-hour glucose >11.1 mmol/l) at baseline and follow-up. The levels of alpha-hydroxybutyrate (2-HB) and linoleoyl-GPC (L-GPC) were measured in fasting plasma samples collected at baseline and 3 years from these Group 1 and Group 2 participants as described in Example 5 below.

Statistical Analysis.

Data are given as median and [interquartile range] and mean and standard deviation (Tables 1-3). Multiple linear regression, correlation, and logistic regression analyses were carried out on untransformed data and log-transformed data. Multiple logistic regression tested the independent association of metabolites with progression to dysglycemia (impaired glucose regulation, IGR, or type 2 diabetes, T2D) as defined by fasting plasma glucose and 2 hour postprandial OGTT glucose results. Results are given as the odds ratio and 95% confidence interval (C.I.). Statistical analyses were performed using JMP (JMP, Version 8. SAS Institute Inc., Cary, N.C., 1989-2009).

The baseline anthropometric and metabolic data of the Group 1 participants are given in Table 1A for the 1,115 normal glucose tolerant (NGT) subjects, the 146 impaired glucose regulation (IGR) and the 47 type 2 diabetic (T2DM) subjects. Fasting plasma glucose levels, 2-hour plasma glucose concentrations (based on the OGTT), and fasting plasma insulin concentrations were progressively higher in IGR, and T2DM, than in NGT subjects while β-cell glucose sensitivity was progressively lower. Across these groups, plasma levels of 2-HB were progressively higher, while plasma LGPC concentrations showed an inverse gradient, the respective highest and lowest levels being seen in the T2DM subjects. Furthermore, β-cell glucose sensitivity, a measure of beta-cell function, was reciprocally related to plasma 2-HB concentrations.

The baseline anthropometric and metabolic data of Group 2 participants are given in Table 1B for the 1,811 NGT subjects and the 642 IGR subjects. As in the Group 1 cohort, fasting plasma glucose levels, 2-hour plasma glucose concentrations (based on the OGTT), and fasting plasma insulin concentrations were higher in IGR subjects, while the insulin/glucose ratio (I/G, from the OGTT) was low in the IGR subjects. Plasma levels of 2-HB were higher in IGR subjects, while plasma LGPC levels were lower.

Analysis of Plasma Samples at Follow Up.

Among the Group 1 participants tested 3 years after the baseline measurements, oral glucose tolerance was still normal in 779 subjects (stable NGT) and had deteriorated in 123 subjects (progressors). At baseline, the subjects that progressed were more β-cell-glucose insensitive, and had higher plasma 2-HB and lower LGPC concentrations (Table 2A). At follow up, 2-HB levels had decreased in stable NGT subjects (by 0.38 [2.01] µg/ml) and increased in the progressors (by 0.42 [2.12] µg/ml), with the difference being significant at the p=0.0003 level. In contrast, LGPC levels had increased in stable NGT (by 0.83 [6.4] µg/ml) and decreased in progressors (by 0.2[4.8] µg/ml), this difference was statistically significant (p<0.05) (Table 2A).

Among the 2,580 Group 2 participants, 151 subjects had developed diabetes at the 9.5-year follow-up visit, as shown in Table 2B. The baseline clinical and metabolic characteristics of these progressors viz. the Group 2 non-progressors were very similar to those of the Group 1 progressors. Beta-cell glucose sensitivity was decreased and plasma 2-HB levels were higher and plasma LGPC levels were lower in the subjects who progressed.

TABLE 1A

Group 1 Cohort: baseline anthropometric and metabolic parameters.[#]

| M quartile | NGT | IGR | T2DM |
|---|---|---|---|
| n | 1115 | 146 | 47 |
| Fasting glucose (mmol/l) | 5.00 ± 0.58 | 5.49 ± 0.67 [+] | 9.28 ± 1.89 [+] |
| 2-hour glucose (mmol/l)° | 5.79 ± 1.08 | 8.15 ± 1.31 [+] | 12.76 ± 2.61 [+] |
| Fasting insulin (pmol/l)° | 41 [28] | 42 [35] [+] | 67 [53] [+] |
| β-GS (pmol·min$^{-1}$·m$^{-2}$·mM$^{-1}$) | 114 [74] | 69 [46] [+] | 32 [35] [+] |
| α-HB (µg/l)° | 4.87 [2.33] | 5.10 [2.55] [+] | 7.42 [2.41] [+] |
| L-GPC (µg/l)° | 13.03 [5.18] | 13.83 [7.73] [+] | 7.34 [3.31] [+] |

[#]entries are mean ± SD or median [IQR]; NGT = normal glucose tolerance; IGR = impaired glucose regulation; β-GS = β-cell glucose sensitivity (from the OGTT); α-HB = α-hydroxybutyrate; L-GPC = linoleoylglycerophosphocholine.
°p < 0.0001 for NGT quartiles by Kruskal-Wallis test
[+] p < 0.05 or less for the difference between IGR and NGT by Mann Whitney test

TABLE 1B

Group 2 Cohort: baseline anthropometric and metabolic parameters.[#]

| | NGT | IGR |
|---|---|---|
| n | 1115 | 642 |
| Fasting glucose (mmol/l) | 5.46 ± 0.42 | 6.04 ± 0.56 [+] |
| 2-hour glucose (mmol/l) | 6.35 ± 0.86 | 7.90 ± 1.45 [+] |
| Fasting insulin (pmol/l) | 55 [35] | 52 [39] [+] |
| IG index (pmol · mM$^{-1}$) | 111 [108] | 78 [81] [+] |
| α-HB (µg/l) | 3.71 [1.49] | 3.95 [1.72] [+] |
| L-GPC (µg/l)° | 14.29 [4.60] | 14.90 [5.15] [+] |

[#]entries are mean ± SD or median [IQR]; NGT = normal glucose tolerance; IGR = impaired glucose regulation; IG index = insulinogenic index (from the OGTT); α-HB = α-hydroxybutyrate; L-GPC = linoleoylglycerophosphocholine.
°p < 0.0001 for NGT quartiles by Kruskal-Wallis test
[+] p < 0.0001 for the difference between IGR and NGT by Mann Whitney test

TABLE 2A

Group 1 Cohort: baseline anthropometric and metabolic parameters by outcome.[#]

| | Stable NGT | Progressors |
|---|---|---|
| N | 779 | 123 |
| Fasting glucose (mmol/l)° | 5.00 ± 0.48 | 5.32 ± 0.46 |
| 2-hour glucose (mmol/l)° | 5.33 ± 1.11 | 6.17 ± 1.34 |
| Fasting insulin (pmol/l)° | 28 [20] | 39 [28] |
| β-GS (pmol · min$^{-1}$ · m$^{-2}$ · mM$^{-1}$)° | 120 [80] | 69 [60] |
| Baseline α-HB (µg/l)° | 4.21 [2.01] | 4.46 [2.12] |
| Follow-up α-HB (µg/l)° | 3.83 [1.73] | 4.88 [2.06] |
| Baseline L-GPC (µg/l)° | 15.41 [6.60] | 13.29 [5.23] |
| Follow-up L-GPC (µg/l)° | 16.24 [7.03] | 13.02 [6.60] |

[#]entries are mean ± SD or median [IQR]; Stable NGT = subjects whose glucose tolerance was normal both at baseline and follow up; Progressors = subjects who progressed to dysglycemia; β-GS = β-cell glucose sensitivity (from the OGTT); α-HB = α-hydroxybutyrate; L-GPC = linoleoylglycerophosphocholine.
°p < 0.0001 by Mann Whitney test

TABLE 2B

Group 2 Cohort: baseline anthropometric and metabolic parameters by outcome.[#]

| | Non-progressors (Stable NGT) | Progressors |
|---|---|---|
| N | 2429 | 151 |
| Fasting glucose (mmol/l)° | 5.52 ± 0.56 | 5.85 ± 0.63 |
| 2-hour glucose (mmol/l)° | 6.15 ± 1.49 | 7.45 ± 1.88 |
| Fasting insulin (pmol/l)° | 41 [29] | 59 [48] |
| IG index (pmol · mM$^{-1}$)° | 89 [95] | 71 [63] |
| α-HB (µg/l)° | 3.49 [1.55] | 3.83 [1.62] |
| L-GPC (µg/l)° | 15.92 [5.48] | 14.00 [3.56] |

[#]entries are mean ± SD or median [IQR]; Progressors = subjects who progressed to type 2 diabetes; IG index = insulinogenic index (from the OGTT); α-HB = α-hydroxybutyrate; L-GPC = linoleoylglycerophosphocholine.
°p < 0.0001 by Mann Whitney test

Example 3

Correlation of Beta-Cell Function Biomarkers with Indices of Beta-Cell Function Studies were performed on three independent cohorts described in Examples 1 and 2 to determine if the biomarkers associated with beta-cell function could provide a surrogate for currently used beta-cell function indices. In these studies, the biomarkers AHB and LGPC were shown to correlate with beta-cell function as measured by currently available beta-cell indices: the beta-cell glucose sensitivity measurement (pmol·min−1·m−2·mM−1), the insulinogenic index (calculated as the change in insulin concentration (ΔI) (AUC) divided by the change in glucose concentration (ΔG) (AUC) from 0 to 30 min and from 0 to 120 min), or the IS/IR Disposition Index (calculated as insulin secretion/insulin resistance (disposition) index ($\Delta I_{0-120}/\Delta G_{0-120} \times$ Matsuda index) (MI) during OGTT; $\Delta ISR_{0-120}/\Delta G_{0-120} \times MI$).

The biomarkers of beta-cell function correlated with beta cell function as measured by the each of these indices. For the beta-cell glucose sensitivity measurement, the partial correlation of AHB was −0.11 (p=0.0002). For the insulinogenic index, the LGPC correlation was −0.178 (p<0.005) for AHB and 0.127 (p=0.009) for LGPC. For the IS/IR Disposition Index ($\Delta ISR_{0-120}/\Delta G_{0-120} \times MI$), the AHB correlation was −0.224 (p<0.005) and the LGPC correlation was 0.244 (p<0.005) and r=0.830 (p=2.9282e-111) when AHB and LGPC were used in an algorithm comprised of AHB, LGPC, oleate and insulin.

Example 4

Monitoring Beta-Cell Function in Response to Therapeutic Intervention

Monitoring Change in Beta-Cell Function Following Bariatric Surgery Using Beta-Cell Biomarkers.

To demonstrate the utility of the biomarkers of beta-cell function to monitor changes in beta-cell function following therapeutic intervention, the biomarker levels were measured in subjects that had received therapeutic bariatric surgery for treatment of type 2 diabetes.

This first study group included 26 morbidly obese subjects (21 women and 5 men, age 47±8 years, BMI=50.8±7.1 kg/m$^2$) whose beta cell function was determined using the OGTT-based index before and 1 year after Roux-en-Y gastric bypass surgery. 2-Hydroxybutyrate levels decreased as beta-cell function increased in these subjects. For many subjects, beta-cell function improved prior to weight loss and 2-Hydroxybutyrate levels were reduced post-bariatric surgery and the reduction was more pronounced following weight loss.

In a second study, the biomarkers and beta-cell function were determined in subjects receiving Roux-en-Y gastric bypass surgery or Bilio-pancreatic diversion (BPD) surgery. The results are illustrated in FIG. 1, which shows the relationship between AHB (top) and L-GPC (bottom) and how these biomarkers change in individuals who undergo bariatric surgery by one of two techniques, either the Roux en Y bypass or the BPD technique. Both types of therapeutic surgery result in increased beta-cell function as assessed by the beta-cell glucose sensitivity index. The results are illustrated in FIG. 1, top panel. Consistent with the improvement in beta-cell function after surgery, the levels of 2-HB decreased following therapeutic surgery, as shown in FIG. 1, middle panel. In addition, the levels of L-GPC increased following therapeutic surgery as illustrated in FIG. 1, bottom panel.

Monitoring Change in Beta-Cell in Response to Pioglitazone (PIO) Therapy Using Beta-Cell Biomarkers.

In another study, the relationship between changes in the IS/IR Disposition index and changes in the levels of the beta-cell function biomarkers, AHB and LGPC following drug treatment were determined. The study cohort consisted of 431 IGT subjects (FPG=105, 2-h PG [OGTT]=168, HbA1C=5.5%) who were randomized to pioglitazone (45 mg/day) or placebo and followed for 2.4 years. Fasted plasma samples were analyzed at baseline and study end for AHB, LGPC, insulin, HbA1c and Matsuda index. The changes in the levels of the AHB were decreased in response to PIO for the patients that responded to the drug therapy and were increased in the subjects that did not respond and became type 2 diabetic. The levels of L-GPC increased in response to PIO for the patients that responded to the drug therapy and were decreased in the subjects that did not respond and became type 2 diabetic. The data is presented in Table 3. The correlation with the Matsuda index was −0.178 ($p<0.005$) for AHB and 0.127 ($p=0.009$) for LGPC.

TABLE 3

| Biomarker Analyte | Fold change Before and after PIO | p-value | Fold change NGT vs T2D at study end | p-value |
|---|---|---|---|---|
| α-HB | 0.90 ↓ | 0.001 | 1.39 ↑ | <0.005 |
| Linoleoyl-GPC | 1.21 ↑ | <0.005 | 0.82 ↓ | 0.002 |

Example 5

Targeted Assays for the Determination of the Level of Biomarkers in Human Plasma by LC-MS-MS A method for measuring each of the biomarkers listed in Table 4 in EDTA human plasma was developed. Human plasma samples were spiked with internal standards and subjected to protein precipitation as described below. Following centrifugation, the supernatant was removed and injected onto a Waters Acquity/Thermo Quantum Ultra LC-MS-MS system using four different chromatographic systems (column/mobile phase combinations).

The peak areas of the respective parent or product ions were measured against the peak area of the respective internal standard parent or product ions. Quantitation was performed using a weighted linear least squares regression analysis generated from fortified calibration standards prepared immediately prior to each run.

Samples were prepared by adding study samples to individual wells of a 96-well plate. In addition, calibration, blank sample, blank-IS samples, and quality control samples were also included in the 96-well plate. Calibration standards were prepared by adding Combined Calibration Spiking Solutions to water. Calibration standard target concentrations for the various compounds are indicated in Table 5B. Then, acetonitrile/water/ethanol (1:1:2) was added to each of the wells, and a combined internal standard working solution was added to each of the study samples, as well as to the control, calibration standards, and the blank-IS sample. Methanol was added to each sample, shaken vigorously for at least 2 minutes and inverted several times to ensure proper mixture. The samples were then centrifuged at 3000 rpm for 5 minutes at room temperature until a clear upper layer was produced. The clear organic supernatant was transferred to a clean autosampler vial and used for analysis by LC-MS-MS as provided below.

Instrument Conditions for LC-MS-MS:

Compound Set 1 (palmitate (16:0), docosatetraenoic acid, oleate (18:1(n–9))+1359, stearate (18:0), margarate (17:0), linoleate (18:2(n–6)), linolenate (18:2(n–6)), pamitoleic acid, cis-10-heptadecenoic acid):

Mass Spec Conditions for Compound Set 1
  Source Type: HESI source
  Monitor: Selected Reaction Monitoring (SRM), negative mode Chromatographic Conditions for Compound Set 1
  Mobile Phase A1: Water/Ammonium Bicarbonate, 500:1
  Mobile Phase B1: ACN/MeOH (1:1)

Isocratic:

| Time [min] | % A | % B | Flow [mL/min] |
|---|---|---|---|
| 0 | 15 | 85 | 0.5 |

HPLC Column Acquity C 18 BEH, 1.7 micron 2.1 × 100 mm, Waters

Target Needle Wash Procedure
  Use Isopropanol with a target flush volume of 0.500 mL for strong solvent wash and water for the weak solvent wash post-wash.

Compound Set 2 (2-hydroxybutyrate, 3-methyl-2-oxobutyrate, 3-hydroxybutyrate):

Mass Spec Conditions for Compound Set 2
  Source Type: HESI source
  Monitor: Selected Reaction Monitoring (SRM), negative mode Chromatographic Conditions for Compound Set 2 (
  Mobile Phase A2: Water 0.01% Formic acid
  Mobile Phase B1: ACN/MeOH (1:1)

Gradient:

| Time [min] | % A | % B | Flow [mL/min] | Profile |
|---|---|---|---|---|
| 0 | 99 | 1 | 0.4 | |
| 1.0 | 60 | 40 | 0.4 | 6 |
| 1.4 | 60 | 40 | 0.4 | 6 |
| 1.5 | 99 | 1 | 0.4 | 6 |

HPLC Column: Acquity C 18 BEH, 1.7 micron 2.1 × 100 mm, Waters

Target Needle Wash Procedure
  Use Isopropanol with a target flush volume of 0.500 mL for strong solvent wash and water for the weak solvent wash post-wash.

Compound Set 3 (linoleoyl-lyso-GPC, oleoyl-lyso-GPC, palmitoyl-lyso-GPC, stearoyl-lyso-GPC, octanoyl carnitine, decanoyl carnitine, creatine, serine, arginine, glycine, betaine, glutamic acid, threonine, tryptophan, gamma-glutamyl-leucine, glutamyl-valine):
Mass Spec Conditions for Compound Set 3
  Source Type: HESI source
  Monitor: Selected Reaction Monitoring (SRM), positive mode
Chromatographic Conditions for Compound Set 3
  Mobile Phase A2 Water 0.01% Formic acid
  Mobile Phase B2 ACN/Water (700:300), 3.2 g Ammonium formate (=50 mM)
Gradient:

| Time [min] | % A2 | % B2 | Flow [mL/min] | Profile |
|---|---|---|---|---|
| 0 | 98 | 2 | 0.5 | |
| 0.5 | 98 | 2 | 0.5 | 6 |
| 1.0 | 10 | 90 | 0.5 | 6 |
| 2.0 | 10 | 90 | 0.5 | 6 |
| 2.1 | 98 | 2 | 0.6 | 6 |

A2 = Water 0.01% Formic acid,
B2 = ACN/Water (700:300), 3.2 g Ammonium formate (=50 mM)
HPLC Column Biobasic SCX, 5 micron 2.1 × 50 mm, Thermo Target Needle Wash Procedure
  Use Isopropanol with a target flush volume of 0.500 mL for strong solvent wash and water for the weak solvent wash post-wash.
Compound Set 4 (1,5-Anhydroglucitol):
Mass Spec Conditions for Compound Set 4 (1,5-Anhydroglucitol)
  Source Type: HESI source
  Monitor: Selected Reaction Monitoring (SRM), negative mode
Chromatographic Conditions for Compound Set 4 (1,5-Anhydroglucitol)
  Mobile Phase A1 Water/Ammonium Bicarbonate, 500:1
  Mobile Phase B1 ACN/MeOH (1:1)

Isocratic

| Time [min] | % A | % B | Flow [mL/min] | Profile |
|---|---|---|---|---|
| 0 | 15 | 85 | 0.5 | |

HPLC Column: Acquity C 18 BEH, 1.7 micron 2.1 × 100 mm, Waters

Target Needle Wash Procedure
  Use Isopropanol with a target flush volume of 0.500 mL for strong solvent wash and water for the weak solvent wash post-wash.

TABLE 4

| Biomarkers |
|---|
| linoleoyl-lyso-GPC |
| 2-hydroxybutyrate |
| oleate (18:1(n-9)) + 1359 |
| stearate (18:0) |
| margarate (17:0) |
| linoleate (18:2(n-6)) |
| linolenate (18:2(n-6)) |
| pamitoleic acid |
| palmitate (16:0) |
| oleoyl-lyso-GPC |
| palmitoyl-lyso-GPC |
| octanoyl carnitine chloride |
| decanoyl carnitine chloride |
| docosatetraenoic acid |
| 3-methyl-2-oxobutyrate |
| 3-hydroxybutyrate |
| 1,5-anhydroglucitol |
| Creatine |
| Serine |
| Arginine |
| Glycine |
| Betaine |
| glutamic acid |
| Threonine |
| Tryptophan |
| Gamma-glutamyl-leucine |
| Glutamyl-valine |
| Stearoyl-lyso-GPC |
| Cis-10-Heptadecenoic acid |

TABLE 5A

| | Analyte Reference Compound | Ion Monitored/ Transition | Internal Standard Reference Compound | Ion Monitored/ Transition |
|---|---|---|---|---|
| 1 | palmitate (16:0) | 255.3 ->255.3 | palmitic acid $^{13}C_{16}$ | 271.3 ->271.3 |
| 2 | docosatetraenoic acid | 331.3 ->331.3 | palmitic acid $^{13}C_{16}$ | |
| 3 | oleate (18:1(n-9)) + 1359 | 281.3 ->281.3 | oleic acid $^{13}C_{18}$ | 299.3 ->299.3 |
| 4 | stearate (18:0) | 283.3 ->283.3 | octadecanoic acid-18,18,18-$D_3$ | 286.3 ->286.3 |
| 5 | margarate (17:0) | 269.3 ->269.3 | heptadecanoic acid-17,17,17-$D_3$ | 272.3 ->272.3 |
| 6 | linoleate (18:2(n-6)) | 277.3 ->277.3 | linoleic acid $^{13}C_{18}$ | 297.3 -> |
| 7 | linolenate (18:2(n-6)) | 279.3 ->279.3 | linolenic acid $^{13}C_{18}$ | 295.3 ->295.3 |
| 8 | pamitoleic acid | 253.2 ->253.2 | linolenic acid $^{13}C_{18}$ | |
| 9 | linoleoyl-lyso-GPC | 520.6 ->184.1 | linoleoyl-lyso-GPC-(N,N,N-triMe-$D_9$) | 529.6 ->193.1 |
| 10 | oleoyl-lyso-GPC | 522.6 ->184.1 | linoleoyl-lyso-GPC-(N,N,N-triMe-$D_9$) | |
| 11 | palmitoyl-lyso-GPC | 496.6 ->184.1 | linoleoyl-lyso-GPC-(N,N,N-triMe-$D_9$) | |
| 12 | octanoyl carnitine chloride | 288.4 ->85.1 | octanoyl carnitine-(N-methyl-$D_3$) HCl | 291.4 ->85.1 |

TABLE 5A-continued

|    | Analyte Reference Compound | Ion Monitored/ Transition | Internal Standard Reference Compound | Ion Monitored/ Transition |
|----|---|---|---|---|
| 13 | decanoyl carnitine chloride | 316.4 ->85.1 | decanoyl carnitine-(N-methyl-$D_3$) HCl | 319.4 ->85.1 |
| 14 | 2-hydroxybutyrate | 103.1 ->57.1 | Na-2-hydroxybutyrate-2,3,3-$D_3$ | 106.1 ->59.1 |
| 15 | 3-methyl-2-oxobutyrate | 115.1 ->71.1 | 3-methyl-2oxobutyrate-$D_7$ | 122.1 ->78.1 |
| 16 | 3-hydroxybutyrate | 103.1 ->59.1 | Na-3-hydroxybutyrate-3,4,4,4-$D_4$ | 107.1 ->59.1 |
| 17 | 1,5-anhydroglucitol | 163.1 ->101.1 | 1,5-anhydroglucitol-1,5-$^{13}C_6$ | 169.1 ->105.1 |
| 18 | creatine | 132.1 ->90.1 | creatine (Methyl)-$D_3$ | 135.1 ->93.1 |
| 19 | serine | 106.1 -60.1 | serine-2,3,3-$D_3$ | 109.1 ->63.1 |
| 20 | arginine | 175.1 ->70.1 | arginine-$^{13}C_6$ | 181.1 ->74.1 |
| 21 | glycine | 76.1 ->30.1 | glycine $^{13}C_2$-$^{15}N$ | 79.1 ->32.1 |
| 22 | betaine | 118.1 ->58.1 | betaine-$D_9$ (N,N,N-trimethyl-$D_9$) | 127.1 ->66.1 |
| 23 | glutamic acid | 148.1 ->84.1 | glutamic acid-2,3,3,4,4-$D_5$ | 153.1 ->88.1 |
| 24 | threonine | 120 ->74.1 | threonine-$^{13}C_4$-$^{15}N$ | 125 ->78.1 |
| 25 | tryptophan | 205.2 ->146.1 | tryptophan-$D_5$ | 210.2 ->151.1 |
| 26 | Gamma-glutamyl-leucine | 261.2 ->132.1 | betaine-$D_9$ (N,N,N-trimethyl-$D_9$) | 127.1 ->66.1 |
| 27 | Glutamyl-valine | 247.2 ->118.1 | betaine-$D_9$ (N,N,N-trimethyl-$D_9$) | 127.1 ->66.1 |
| 28 | Stearoyl-lyso-GPC | 524.6 ->184.1 | linoleoyl-lyso-GPC-(N,N,N-triMe-$D_9$) | 529.6 ->193.1 |
| 29 | Cis-10-Heptadecenoic acid | 267.3 ->267.3 | palmitic acid $^{13}C_{16}$ | 271.3 ->271.3 |

TABLE 5B

Calibration standard target concentrations

| Reference Standard | STD A, Target conc (ug/mL) | STD B, Target conc (ug/mL) | STD C, Target conc (ug/mL) | STD D, Target conc (ug/mL) | STD E, Target conc (ug/mL) | STD F, Target conc (ug/mL) |
|---|---|---|---|---|---|---|
| palmitate (16:0) | 5.000 | 10.000 | 25.000 | 80.000 | 140.000 | 200.000 |
| docosatetraenoic acid | 0.050 | 0.100 | 0.250 | 0.800 | 1.400 | 2.000 |
| oleate (18:1(n-9)) + 1359 | 10.000 | 20.000 | 50.000 | 160.000 | 280.000 | 400.000 |
| stearate (18:0) | 2.500 | 5.000 | 12.500 | 40.000 | 70.000 | 100.000 |
| margarate (17:0) | 0.025 | 0.050 | 0.125 | 0.400 | 0.700 | 1.000 |
| linoleate (18:2(n-6)) | 2.500 | 5.000 | 12.500 | 40.000 | 70.000 | 100.000 |
| linolenate (18:2(n-6)) | 0.150 | 0.300 | 0.750 | 2.400 | 4.200 | 6.000 |
| pamitoleic acid | 1.000 | 2.000 | 5.000 | 16.000 | 28.000 | 40.000 |
| linoleoyl-lyso-GPC | 2.500 | 5.000 | 12.500 | 40.000 | 70.000 | 100.000 |
| oleoyl-lyso-GPC | 2.500 | 5.000 | 12.500 | 40.000 | 70.000 | 100.000 |
| palmitoyl-lyso-GPC | 2.500 | 5.000 | 12.500 | 40.000 | 70.000 | 100.000 |
| octanoyl carnitine chloride | 0.003 | 0.006 | 0.015 | 0.048 | 0.084 | 0.120 |
| decanoyl carnitine chloride | 0.003 | 0.006 | 0.015 | 0.048 | 0.084 | 0.120 |
| 2-hydroxybutyrate | 0.500 | 1.000 | 2.500 | 8.000 | 14.000 | 20.000 |
| 3-methyl-2-oxobutyrate | 0.500 | 1.000 | 2.500 | 8.000 | 14.000 | 20.000 |
| 3-hydroxybutyrate | 0.500 | 1.000 | 2.500 | 8.000 | 14.000 | 20.000 |
| 1,5-anhydroglucitol | 2.000 | 4.000 | 10.000 | 32.000 | 56.000 | 80.000 |
| creatine | 0.500 | 1.000 | 2.500 | 8.000 | 14.000 | 20.000 |
| Serine | 1.250 | 2.500 | 6.250 | 20.000 | 35.000 | 50.000 |
| arginine | 1.250 | 2.500 | 6.250 | 20.000 | 35.000 | 50.000 |
| glycine | 1.250 | 2.500 | 6.250 | 20.000 | 35.000 | 50.000 |
| betaine | 0.500 | 1.000 | 2.500 | 8.000 | 14.000 | 20.000 |
| glutamic acid | 1.000 | 2.000 | 5.000 | 16.000 | 28.000 | 40.000 |
| threonine | 1.250 | 2.500 | 6.250 | 20.000 | 35.000 | 50.000 |
| tryptophan | 0.400 | 0.800 | 2.000 | 6.400 | 11.200 | 16.000 |
| Gamma-glutamyl-leucine | 0.010 | 0.020 | 0.050 | 0.160 | 0.280 | 0.400 |

TABLE 5B-continued

| Reference Standard | STD A, Target conc (ug/mL) | STD B, Target conc (ug/mL) | STD C, Target conc (ug/mL) | STD D, Target conc (ug/mL) | STD E, Target conc (ug/mL) | STD F, Target conc (ug/mL) |
|---|---|---|---|---|---|---|
| Glutamyl-valine | 0.010 | 0.020 | 0.050 | 0.160 | 0.280 | 0.400 |
| Stearoyl-lyso-GPC | 2.500 | 5.000 | 12.500 | 40.000 | 70.000 | 100.000 |
| Cis-10-Heptadecenoic acid | 0.025 | 0.050 | 0.125 | 0.400 | 0.700 | 1.000 |

Example 6

Effects of AHB and LGPC on Beta-Cell Function (Glucose Sensitivity)

Cell Cultures

Clonal INS-1e cells, derived and selected from a parental rat insulinoma INS-1 cell line (University of Geneva, Geneva, Switzerland), were grown in monolayer culture in RPMI 1640 medium containing 11.1 mM glucose. The culture medium was supplemented with 10% heat-inactivated fetal calf serum, 1 mM sodium pyruvate, 10 mM HEPES, 2 mM glutamine, 50 μmol/liter β-mercaptoethanol, 100 U/ml penicillin, and 100 μg/ml streptomycin. Cells were cultured at 37 C in a humidified 95% air-5% $CO_2$ atmosphere. Cells were seeded onto wells at a density of $1.5 \times 10^5$ cells/well at least 96 h before using them in the insulin secretion experiments. Tissue culture reagents were obtained from Life Technologies, Inc. Invitrogen (Basel, Switzerland).

Figure 2:
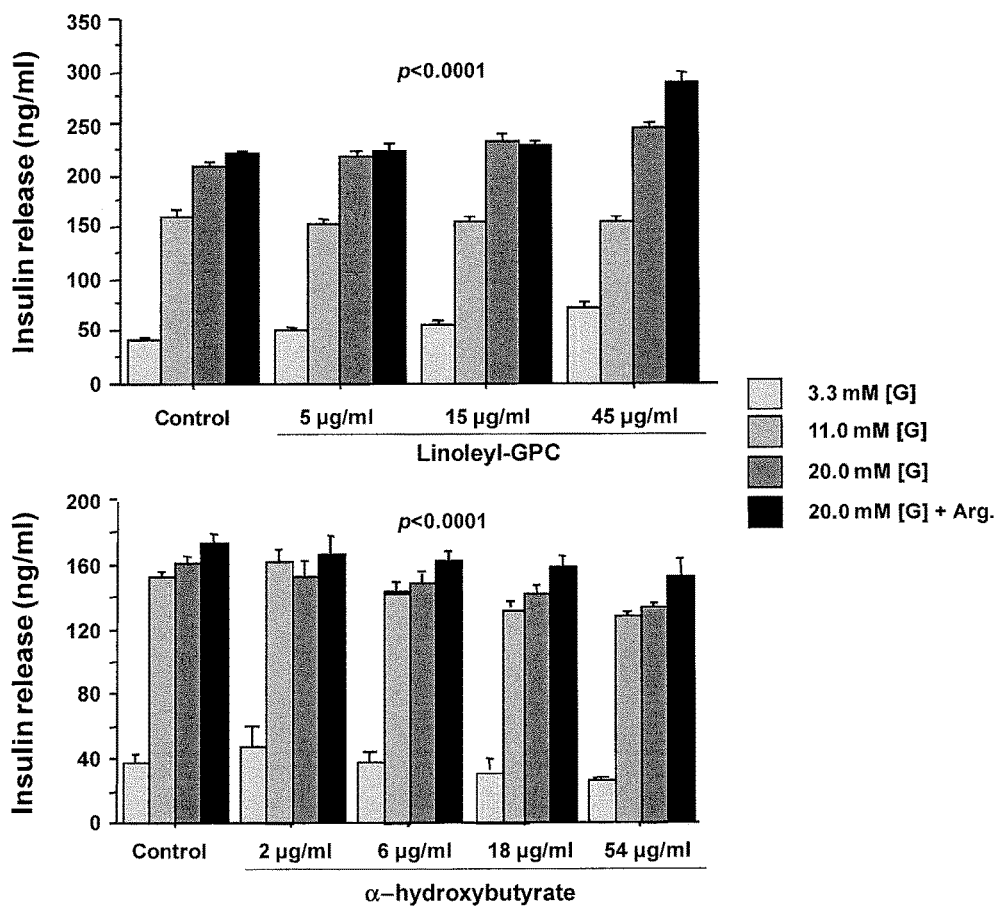
FIG. 2. Effect of addition of various amounts of Linoleoyl-GPC (top panel) or 2-hydroxybutyrate (bottom panel) on glucose-stimulated insulin release in rat pancreatic beta-cells. Addition of Linoleoyl-GPC has a stimulatory effect while 2-hydroxybutyrate has an inhibitory effect on insulin release.

The insulin secretory response to glucose was tested in INS-1e cells. When cells had reached approximately 80% confluence, cells were incubated for 48 h in fresh RPMI 1640 medium containing 11.1 mM glucose, in the presence or absence of different physiological concentrations of metabolites alpha-hydroxybutyrate (2-HB) (Sigma-Aldrich) and linoleoyl-glycerophosphocholine (L-GPC) (Avanti Polar Lipids). Next, cells were maintained for 1 h in glucose-free Krebs-Ringer bicarbonate HEPES buffer containing 135 mm NaCl, 3.6 mm KCl, 5 mm $NaHCO_3$, 0.5 mm Na $H_2PO_4$, 0.5 mm $MgCl_2$, 1.5 mm $CaCl_2$, 10 mm HEPES, and BSA 0.1% (glucose-free; pH 7.4; starvation period) and then washed with glucose-free Krebs-Ringer bicarbonate-HEPES buffer and subsequently incubated for 60 mM with Krebs-Ringer bicarbonate-HEPES buffer containing 3.3, 11, 20 mM glucose, or 20 mM glucose+10 mM arginine. At the end of incubation, supernatants were collected to measure insulin concentration (Linco Research, St. Charles, Mo.). Cellular insulin contents were determined in acid-ethanol extracts. The insulin secretory response to glucose was expressed as the ratio of insulin concentration in the supernatant to the cellular insulin content. The results of these experiments showed that addition of AHB inhibited the glucose stimulated release of insulin from the beta-cells, especially at the higher levels of AHB. In contrast, the addition of LGPC stimulated the glucose stimulated release of insulin from the beta-cells and the stimulation effect was most evident at the highest levels of LGPC. The graphical depiction of the results of the analysis are presented in FIG. 2.

These experiments were also performed as described using human beta-cell lines and similar results were obtained using the highest concentrations of AHB.

While the invention has been described in detail and with reference to specific embodiments thereof, it will be apparent to one skilled in the art that various changes and modifications can be made without departing from the spirit and scope of the invention.

What is claimed is:

1. A method for determining and treating compromised beta-cell function in a human subject, the method comprising:
    extracting small molecules from a plasma sample obtained from the human subject to produce an analytical sample;
    performing chromatography, mass spectrometry, or a combination thereof on the analytical sample to determine the levels of one or more biomarkers selected from the group consisting of 2-hydroxybutyrate (2-HB) and linoleoyl lysophosphatidylcholine (L-LPC/L-GPC);
    determining compromised pancreatic beta-cell function in the subject by comparing the levels of the one or more biomarkers in the sample to functional pancreatic beta-cell reference levels of the one or more biomarkers wherein higher or elevated levels of 2-hydroxybutyrate (2-HB) compared to normal beta-cell reference levels indicate beta-cell dysfunction and lower or decreased levels of linoleoyl lysoglycerophospocholine (L-LPC/L-GPC) compared to normal beta-cell reference levels indicate beta-cell dysfunction; and
    administering an effective treatment to the human subject having compromised beta-cell function, wherein effective treatment comprises one or more of surgical intervention, drug treatment intervention, exercise, early-stage drug treatment, administering a therapeutic agent for compromised beta-cell function, performing bariatric surgery, administering an effective amount of L-LPC or one or more biomarkers that are lowered in a human subject with compromised beta-cell function as compared to a healthy human subject not having compromised beta-cell function.

2. The method of claim 1, wherein comparing comprises generating a pancreatic beta-cell function score for the subject.

3. The method of claim 2, wherein the pancreatic beta-cell function score places the subject in a range of pancreatic beta-cell function.

4. The method of claim 2, wherein the pancreatic beta-cell function score is used to determine the probability that the subject has compromised pancreatic beta-cell function.

5. The method of claim 2, wherein the pancreatic beta-cell function score is used to identify subjects with compromised pancreatic beta-cell function for treatment.

* * * * *